(12) United States Patent
Girard et al.

(10) Patent No.: US 8,109,868 B2
(45) Date of Patent: *Feb. 7, 2012

(54) CARDIAC SUPPORT DEVICE

(75) Inventors: Michael J. Girard, Lino Lakes, MN (US); James Edward Shapland, Vadnais Heights, MN (US); Donald F. Palme, II, Princeton, MN (US)

(73) Assignee: Mardil, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,965

(22) Filed: Jul. 6, 2010

(65) Prior Publication Data
US 2010/0274075 A1 Oct. 28, 2010

Related U.S. Application Data

(63) Continuation of application No. 10/984,459, filed on Nov. 8, 2004, now abandoned, which is a continuation of application No. 10/165,504, filed on Jun. 7, 2002, now Pat. No. 6,951,534, which is a continuation-in-part of application No. 09/593,251, filed on Jun. 13, 2000, now Pat. No. 6,482,146.

(51) Int. Cl.
*A61F 2/00* (2006.01)

(52) U.S. Cl. ........................................................ 600/37

(58) Field of Classification Search .............. 600/16–18, 600/37; 128/897–899
See application file for complete search history.

(56) References Cited

U.S. PATENT DOCUMENTS

| 3,983,863 | A |   | 10/1976 | Janke et al. |
|---|---|---|---|---|
| 4,048,990 | A |   | 9/1977 | Goetz |
| 4,428,375 | A |   | 1/1984 | Ellman |
| 4,630,597 | A |   | 12/1986 | Kantrowitz et al. |
| 4,690,134 | A |   | 9/1987 | Snyders |
| 4,821,723 | A |   | 4/1989 | Baker, Jr. et al. |
| 4,878,890 | A |   | 11/1989 | Bilweis |
| 4,932,972 | A |   | 6/1990 | Dunn et al. |
| 4,936,857 | A |   | 6/1990 | Kulik |
| 4,957,477 | A |   | 9/1990 | Lundback |
| 4,973,300 | A |   | 11/1990 | Wright |
| 4,976,730 | A |   | 12/1990 | Kwan-Gett |
| 4,984,584 | A | * | 1/1991 | Hansen et al. ................. 128/898 |
| 5,057,117 | A |   | 10/1991 | Atweh |
| 5,087,243 | A |   | 2/1992 | Avitall |
| 5,131,905 | A |   | 7/1992 | Grooters |

(Continued)

FOREIGN PATENT DOCUMENTS

DE 295 17 393 U1 2/1996

(Continued)

OTHER PUBLICATIONS

"Supplement to Circulation", Abstracts from the 68th Scientific Sessions, vol. 92, No. 8, 2 pages (Oct. 15, 1995).

(Continued)

*Primary Examiner* — Samuel Gilbert
(74) *Attorney, Agent, or Firm* — The Nath Law Group; Laurie A. Axford

(57) ABSTRACT

A highly compliant and elastic cardiac support device is provided. The device is constructed from a biocompatible material is applied to an external surface of a heart. The device can be used to resist dilatation of the heart, to provide acute wall support, or to enhance reduction in the size of the heart using stored potential energy, without interfering with systolic contraction.

14 Claims, 15 Drawing Sheets

U.S. PATENT DOCUMENTS

| | | | |
|---|---|---|---|
| 5,150,706 A | 9/1992 | Cox et al. | |
| 5,186,711 A | 2/1993 | Epstein | |
| 5,192,314 A | 3/1993 | Daskalakis | |
| 5,256,132 A | 10/1993 | Snyders | |
| 5,290,217 A | 3/1994 | Campos | |
| 5,356,432 A | 10/1994 | Rutkow et al. | |
| 5,383,840 A | 1/1995 | Heilman et al. | |
| 5,385,156 A | 1/1995 | Oliva | |
| 5,405,360 A | 4/1995 | Tovey | |
| 5,429,584 A | 7/1995 | Chiu | |
| 5,507,779 A | 4/1996 | Altman | |
| 5,524,633 A | 6/1996 | Heaven et al. | |
| 5,558,617 A | 9/1996 | Heilman et al. | |
| 5,603,337 A | 2/1997 | Jarvik | |
| 5,647,380 A | 7/1997 | Campbell et al. | |
| 5,702,343 A * | 12/1997 | Alferness | 600/37 |
| 5,713,954 A | 2/1998 | Rosenberg et al. | |
| 5,800,528 A | 9/1998 | Lederman et al. | |
| 5,961,440 A | 10/1999 | Schweich, Jr. et al. | |
| 5,990,378 A | 11/1999 | Ellis | |
| 6,042,536 A | 3/2000 | Tihon et al. | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,218 A | 6/2000 | Alferness | |
| 6,085,754 A | 7/2000 | Alferness et al. | |
| 6,123,662 A | 9/2000 | Alferness et al. | |
| 6,126,590 A | 10/2000 | Alferness | |
| 6,155,972 A | 12/2000 | Nauertz et al. | |
| 6,165,121 A | 12/2000 | Alferness | |
| 6,165,122 A | 12/2000 | Alferness | |
| 6,174,279 B1 | 1/2001 | Girard | |
| 6,193,648 B1 | 2/2001 | Krueger | |
| 6,241,654 B1 | 6/2001 | Alferness | |
| 6,360,749 B1 | 3/2002 | Jayaraman | |
| 6,375,608 B1 | 4/2002 | Alferness | |
| 6,402,680 B2 | 6/2002 | Mortier et al. | |
| 6,416,459 B1 | 7/2002 | Haindl | |
| 6,425,856 B1 | 7/2002 | Shapland et al. | |
| 6,432,039 B1 | 8/2002 | Wardle | |
| 6,482,146 B1 | 11/2002 | Alferness et al. | |
| 6,517,570 B1 | 2/2003 | Lau et al. | |
| 6,537,203 B1 | 3/2003 | Alferness et al. | |
| 6,544,168 B2 | 4/2003 | Alferness | |
| 6,572,533 B1 | 6/2003 | Shapland et al. | |
| 6,582,355 B2 | 6/2003 | Alferness et al. | |
| 6,587,734 B2 | 7/2003 | Okuzumi | |
| 6,612,978 B2 | 9/2003 | Lau et al. | |
| 6,645,139 B2 | 11/2003 | Haindl | |
| 6,663,558 B2 | 12/2003 | Lau et al. | |
| 6,682,474 B2 | 1/2004 | Lau et al. | |
| 6,682,475 B2 | 1/2004 | Cox et al. | |
| 6,682,476 B2 | 1/2004 | Alferness et al. | |
| 6,695,769 B2 | 2/2004 | French et al. | |
| 6,902,524 B2 | 6/2005 | Alferness et al. | |
| 6,951,534 B2 | 10/2005 | Girard et al. | |
| 7,022,063 B2 | 4/2006 | Lau et al. | |
| 7,276,022 B2 | 10/2007 | Lau et al. | |
| 7,404,793 B2 | 7/2008 | Lau | |
| 7,410,461 B2 | 8/2008 | Lau et al. | |
| 2002/0019580 A1 | 2/2002 | Lau et al. | |
| 2002/0045798 A1 | 4/2002 | Lau et al. | |
| 2004/0210104 A1 | 10/2004 | Lau et al. | |
| 2005/0033109 A1 | 2/2005 | Lau et al. | |
| 2005/0085688 A1 | 4/2005 | Girard et al. | |
| 2005/0228217 A1 | 10/2005 | Alferness et al. | |
| 2010/0185050 A1 | 7/2010 | Alferness et al. | |

FOREIGN PATENT DOCUMENTS

| | | |
|---|---|---|
| EP | 0 280 564 | 8/1988 |
| JP | 60-203250 | 10/1985 |
| JP | 01-145066 | 6/1989 |
| JP | 2271829 | 11/1990 |
| SU | 1009457 | 4/1983 |
| WO | WO 96/31175 | 10/1996 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/67985 | 9/2001 |

OTHER PUBLICATIONS

Capomolla, S. et al., "Dobutamine and nitroprusside infusion in patients with severe congestive heart failure: Hemodynamic improvement by discordant effects on mitral regurgitation, left atrial function, and ventricular function", American Heart Journal, pp. 1089-1098 (Dec. 1997).

Capouya, E. et al., "Girdling Effect of Nonstimulated Cardiomyoplasty on Left Ventricular Function", Ann Thorac. Surg., vol. 56, pp. 867-871 (1993).

Cohn, J., "The Management of Chronic Heart Failure", The New England Journal of Medicine, vol. 335, No. 7, pp. 490-498 (Aug. 15, 1996).

Coletta, C. et al., Prognostic value of left ventricular volume response during dobutamine stress echocardiography:, European Heart Journal, vol. 18, pp. 1599-1605 (Oct. 1997).

Guasp, F., "Una protesis contentiva para el tratamiento de la miocardiopatia dilatada", Revista Espanola de Cardiologia, vol. 51, No. 7, pp. 521-528 (Jul. 1998).

Kass, D. et al., "Reverse Remodeling From Cardiomyoplasty in Human Heart Failure External Constraint Versus Active Assist", Circulation, vol. 91, No. 9, pp. 2314-2318 (May 1, 1995).

Levin, H. et al., "Reversal of Chronic Ventricular Dilation in Patients With End-Stage Cardiomyopathy by Prolonged Mechanical Unloading", Circulation, vol. 91, No. 11, pp. 2717-2720 (Jun. 1, 1995).

Oh, J. et al., "The Effects of Prosthetic Cardiac Binding and Adynamic Cardiomyoplasty in a Model of Dilated Cardiomyopathy", The Journal of Thoracic and Cardiovascular Surgery, vol. 116, No. 1, pp. 148-153 (Jul. 1998).

Paling, D., "Warp Knitting Technology", Columbine Press, p. 111 (1965).

Vaynblat, M. et al., "Cardiac Binding in Experimental Heart Failure", Ann. Thorac. Surg., vol. 64, 11 pages, (1997).

* cited by examiner

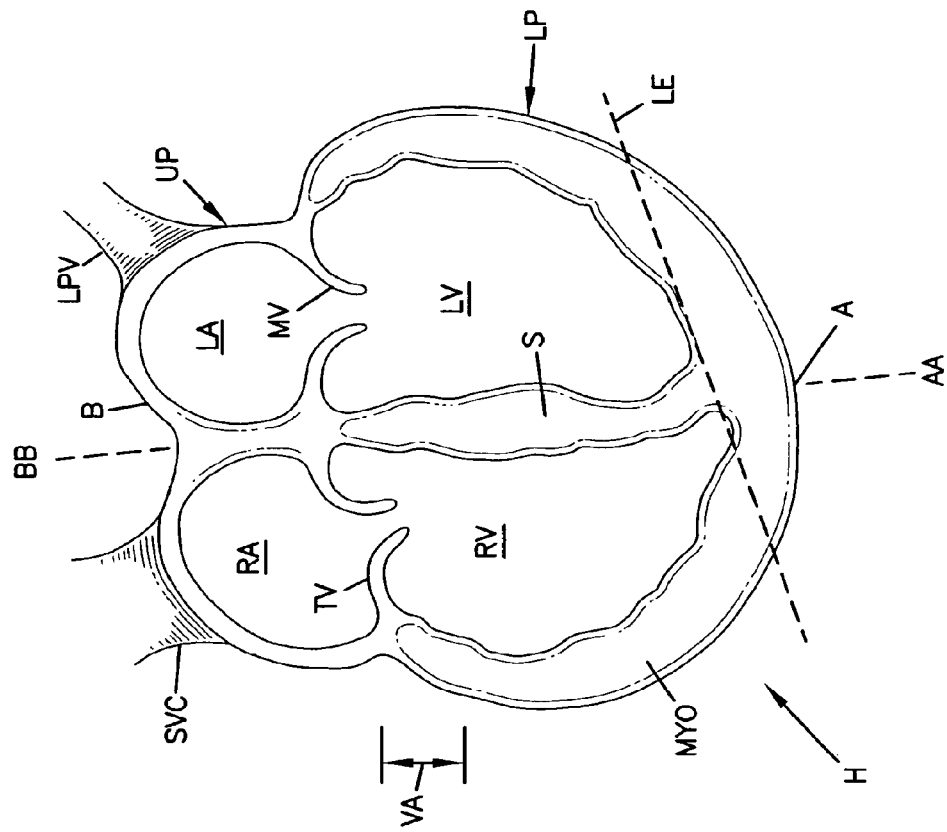
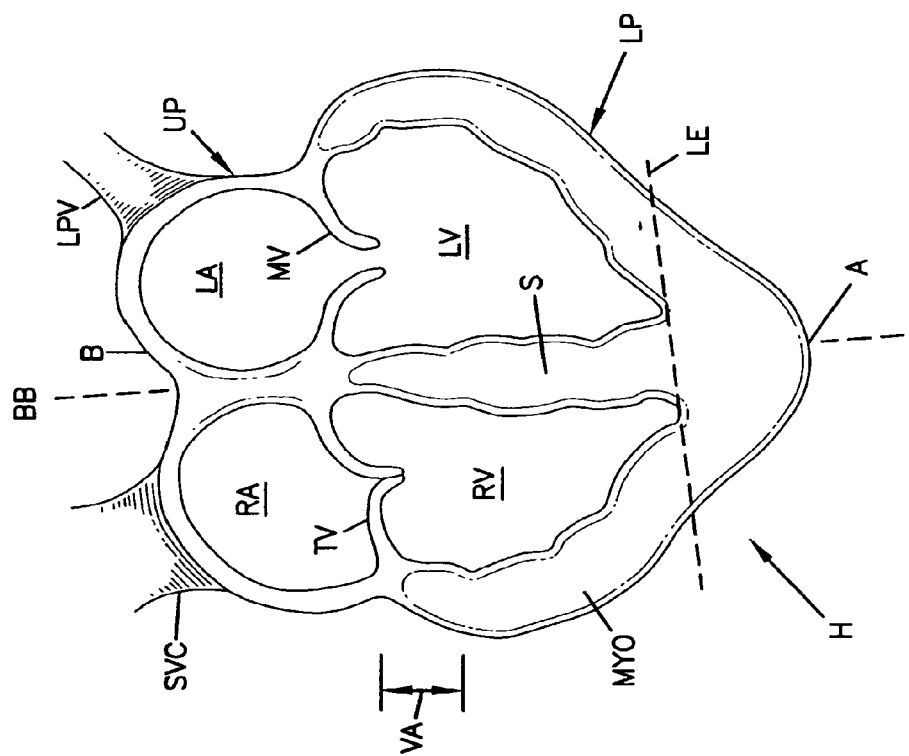

Fig. 12 Device - Elastic Potential Energy

FIG. 15  Cardiac Support Device Mechanical Modes

CARDIAC SUPPORT DEVICE

CROSS REFERENCE TO RELATED APPLICATIONS

This application is a continuation of U.S. patent application Ser. No. 10/984,459, filed Nov. 8, 2004, now abandoned, which is a continuation of Ser. No. 10/165,504 filed Jun. 7, 2002, now U.S. Pat. No. 6,951,534, which is a continuation-in-part of Ser. No. 09/593,251 filed Jun. 13, 2000, now U.S. Pat. No. 6,482,146, which applications are incorporated herein by reference in their entireties and for all purposes.

BACKGROUND OF THE INVENTION

Congestive heart disease is a progressive and debilitating illness characterized by a progressive enlargement of the heart. As the heart enlarges, the heart must perform an increasing amount of work to pump blood each heartbeat needed for metabolism. In time, the heart becomes so enlarged the heart cannot adequately supply blood. An afflicted patient is fatigued, unable to perform even simple exerting tasks and experiences pain and discomfort. Further, as the heart enlarges, the internal heart valves may not adequately close. This may impair the function of the valves and further reduce the heart's ability to supply blood. Importantly, there is no cure for congestive heart disease.

Congestive heart failure has an enormous societal impact. In the United States alone, about five million people suffer from the disease. Alarmingly, congestive heart failure is one of the most rapidly accelerating diseases (about 400,000 new patients in the United States each year). Economic costs of the disease have been estimated at $38 billion annually. Not surprising, substantial effort has been made to find treatments for congestive heart disease.

Cardiomyoplasty is one potential treatment for moderate stage congestive heart disease. In this procedure, the latissimus dorsi muscle (taken from the patient's shoulder) is wrapped around the heart and chronically paced to assist contraction of the heart during systole.

One study speculates that an artificial elastic "sock" could be used in place of the latissimus dorsi in adynamic cardiomyoplasty. Kass et al., "Reverse Remodeling from Cardiomyoplasty in Human Heart Failure," Circulation 91:9, May 1, 1995. Another study demonstrates that Bard Marlex sheets can be used to wrap the heart as a substitute to the latissimus dorsi in adynamic cardiomyoplasty. Oh et al., "The Effects of Prosthetic Cardiac Binding and Adynamic Cardiomyoplasty in a Model of Dilated Cardiomyoplasty," Journal of Thoracic Cardiovascular Surgery, 116:1, July 1998. German Utility Model Patent Application DE 295 17 393 U 1 describes a pericardium prosthesis made from a biocompatible, non-expansible material, or at least hardly expansible material that surrounds the heart to prevent over-expansion of the heart wall. PCT application WO 98/58598 describes an elastic pouch for at least partially enveloping a heart. Commonly assigned U.S. Pat. No. 5,702,343 to Alferness dated Dec. 30, 1997 teaches a jacket to constrain cardiac expansion during diastole. Other teachings include those of commonly assigned U.S. Pat. No. 6,123,662 and those of U.S. Pat. Application Publication No. US 2002/0019580.

SUMMARY OF THE INVENTION

The invention provides a device for treating cardiac disease. According to the invention, a highly compliant and elastic device, constructed from a biocompatible material is applied to an external surface of a heart. The device can be used to resist dilatation of the heart, provide acute wall support, and/or to enhance reduction in the size of the heart using stored potential energy, without interfering with systolic contraction. According to the invention, the device has a compliance that is greater than a compliance of a normal myocardium, more preferably, the device has a compliance greater than a compliance of a normal latissimus dorsi. Considering that stiffness is the inverse of compliance, the uniaxial stiffness of the material is generally less than about 0.5 lbs/in (i.e. load per width of device) when subject to a uniaxial load at a strain of less than 30%, more typically between about 0.05 lbs/in and about 0.2 lbs/in. An alternative way to examine compliance for a device that is applied to an enclosed volume is based on a 3-dimensional volumetric compliance. The 3-dimensional compliance of the device typically allows at least a 3% increase in volume for every 1 mm Hg change in applied device pressure. More typically, the material of the device has a 3-dimensional volumetric compliance between about 5%/mm Hg and about 15%/mm Hg. The device typically has an elastic recovery of at least about 50%, but 70% to 100% is preferable.

In one embodiment, the material of the device is sized to be smaller than the external surface of the heart to which it is applied. In another embodiment, the material of the device is sized to be larger than the external surface of the heart to which it is applied and adapted to be sized by adjustment during implantation. The material can be configured as a jacket for covering both ventricles, one ventricle, ventricles and atria, atria or as a patch covering a portion of a chamber.

The invention also provides a method for treating a cardiac disease. The method includes a step of surgically accessing the heart; and applying a cardiac support device to an external surface of the heart. The method can be used to resist dilatation of the heart, acutely support the wall of the heart, and/or to enhance reduction in a size of the heart using stored potential energy.

BRIEF DESCRIPTION OF THE DRAWINGS

FIG. 2 is a schematic cross-sectional view of a diseased human heart shown during systole;

FIG. 2A is the view of FIG. 2 showing the heart during diastole;

DESCRIPTION OF THE PREFERRED EMBODIMENT

A. Congestive Heart Disease

Figure 1A:
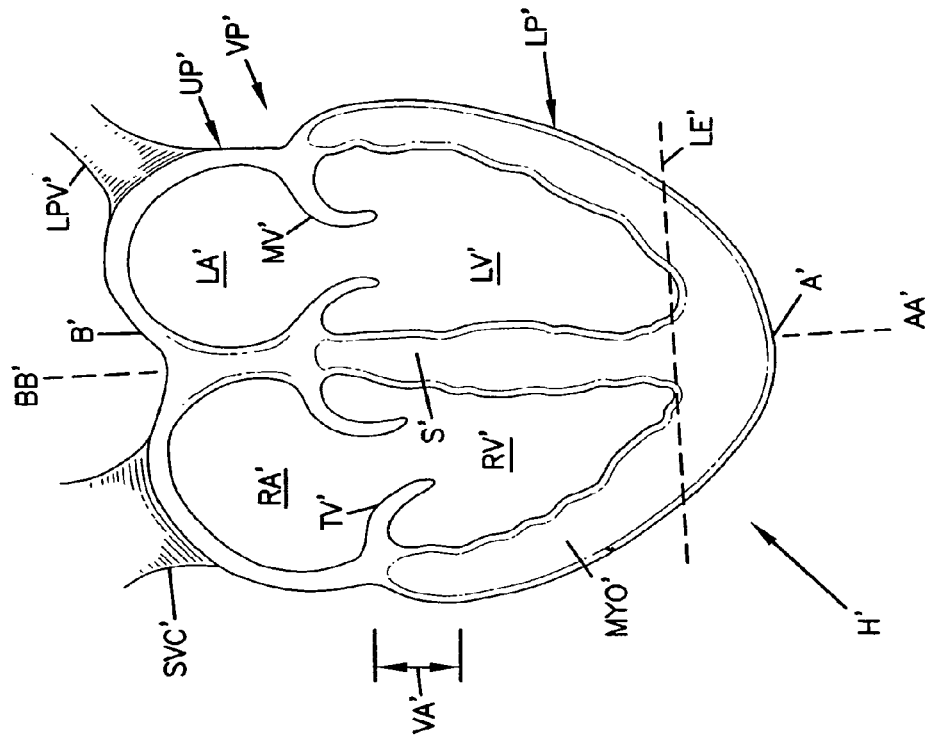
FIG. 1A is the view of FIG. 1 showing the heart during diastole.
Figure 1:
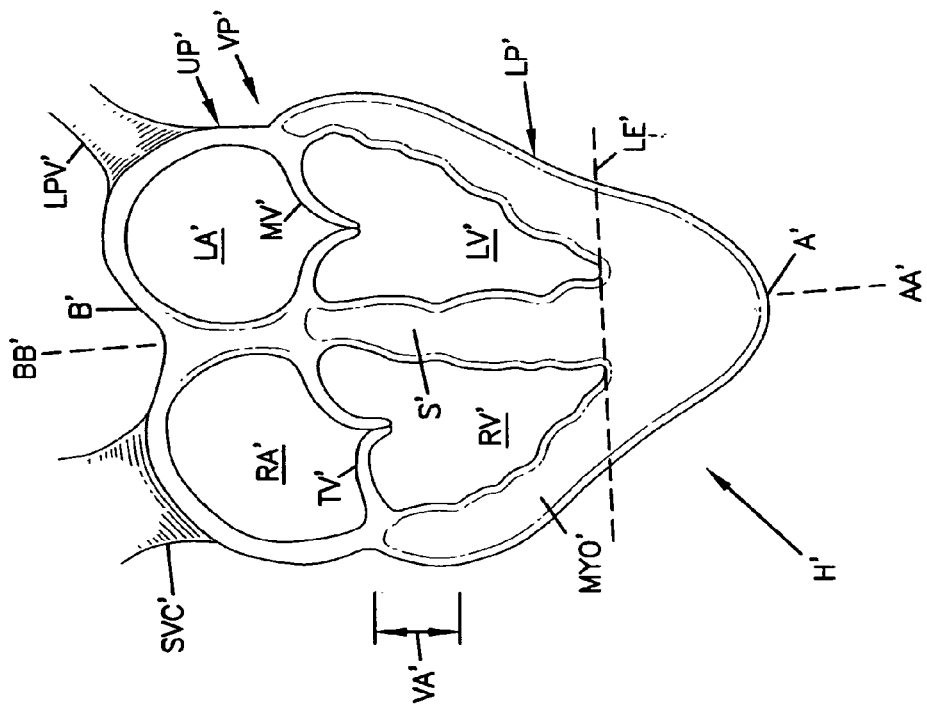
FIG. 1 is a schematic cross-sectional view of a normal, healthy human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure during the ejection phase). In FIG. 1A, the heart H' is shown during diastole (i.e., low left ventricular pressure during the relaxation phase).

The heart H' is a muscle having an outer wall or myocardium MYO' and an internal wall or septum S'. The myocardium MYO', septum S' and valve plane VP' define four internal heart chambers, including a right atrium RA', a left atrium LA', a right ventricle RV' and a left ventricle LV'. The heart H' has a length measured along a longitudinal axis AA'-BB' from an upper end or base B' to a lower end or apex A'.

The heart H' can be visualized as having an upper portion UP' and a lower portion LP', separated by the valve plane VP'. On the external surface of the heart, the upper portion UP' and lower portion LP' meet at a circumferential groove commonly referred to as the A-V groove AVG' right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the A-V groove AVG' and referred to as the valve plane VP' or valvular annulus VA'. The valves TV' and MV' open and close through the beating cycle of the heart H'.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'-BB').

The motion of the heart H' and the variation in the shape of the heart H' during contraction and expansion is complex. The amount of motion varies considerably throughout the heart H', although the external dimension of the heart H' generally reduces from about 4% to about 10% from end diastole to end systole. The motion includes a component which is parallel to the axis AA'-BB' (conveniently referred to as longitudinal expansion or contraction). The motion also includes a component perpendicular to the axis AA'-BB' (conveniently referred to as circumferential expansion or contraction).

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic insufficiency. In contrast to a healthy heart H', the external dimension of the diseased heart H generally reduces from about 4% to about 6% from end diastole to end systole.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 2B:
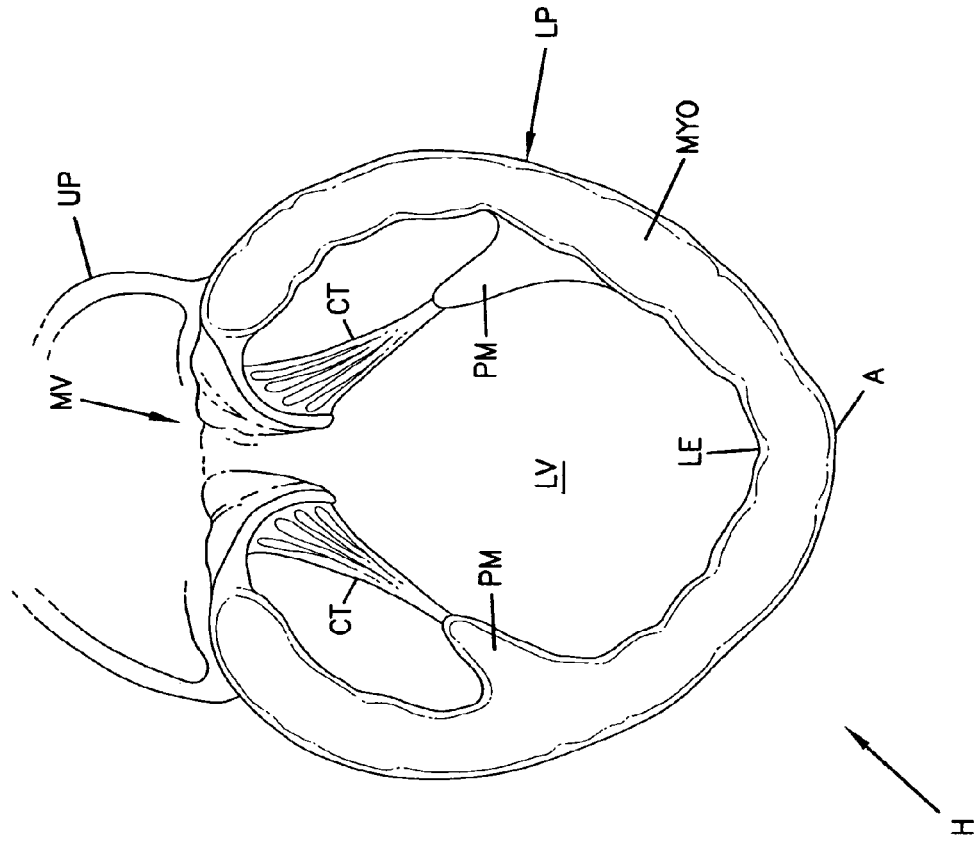
FIG. 2B is the view of FIG. 1B showing a diseased heart.
Figure 1B:
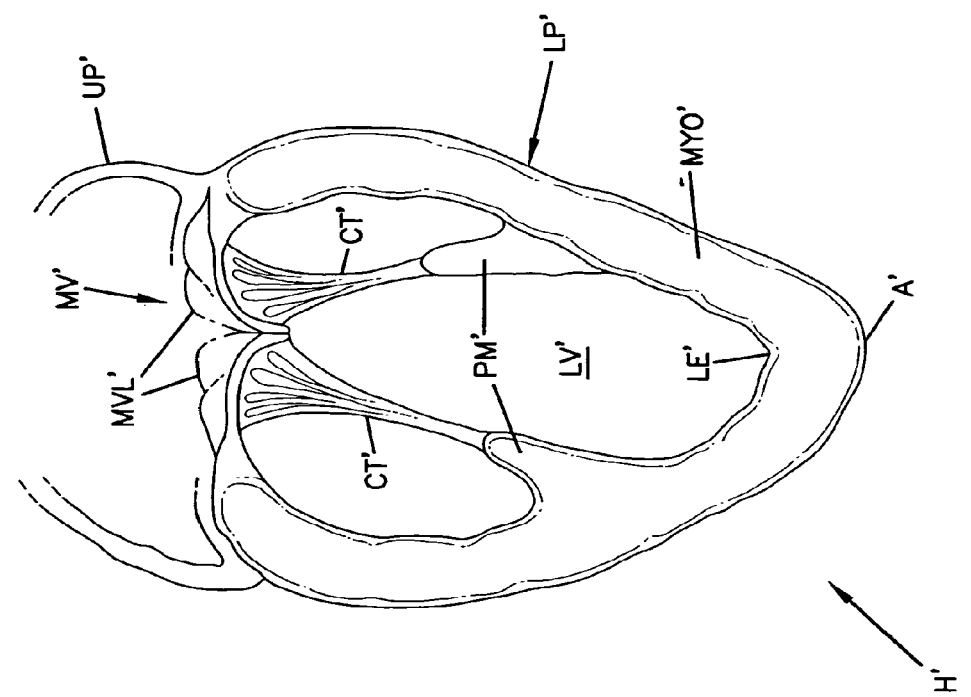
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

B. Cardiac Support Therapy

In general, cardiac support therapy uses a "passive" mechanical implant to support the heart and resist circumferential expansion of the heart during diastole and without actively assisting contraction during systole. Herein, the term "passive" is used to contrast the device with an "active assist" device which uses supplied energy in order to operate, such as devices that assist the heart in pumping blood flow into the aorta, for example, left ventricular assist devices ("LVAD") and total artificial hearts ("TAH"). However the device of the invention does have some mechanical components that involve energy input into the system, and therefore are not entirely "passive." As used herein the term "active" refers to a device wherein energy is added to the system on an ongoing basis. In contrast, a "passive" device, as used herein, may use stored or potential energy. The potential energy stored in the device is generally attributable to energy that is input when the device is fit on the heart, which in part is due to mechanical properties of the device (such as compliance and elasticity). The device can be thought of as having stored energy, similar to a pre-loaded spring. However, in contrast to an "active" device, once the device of the invention is implanted, no additional energy is added continually. The mechanical components of the device that involve energy input are described in detail below.

Figure 3:
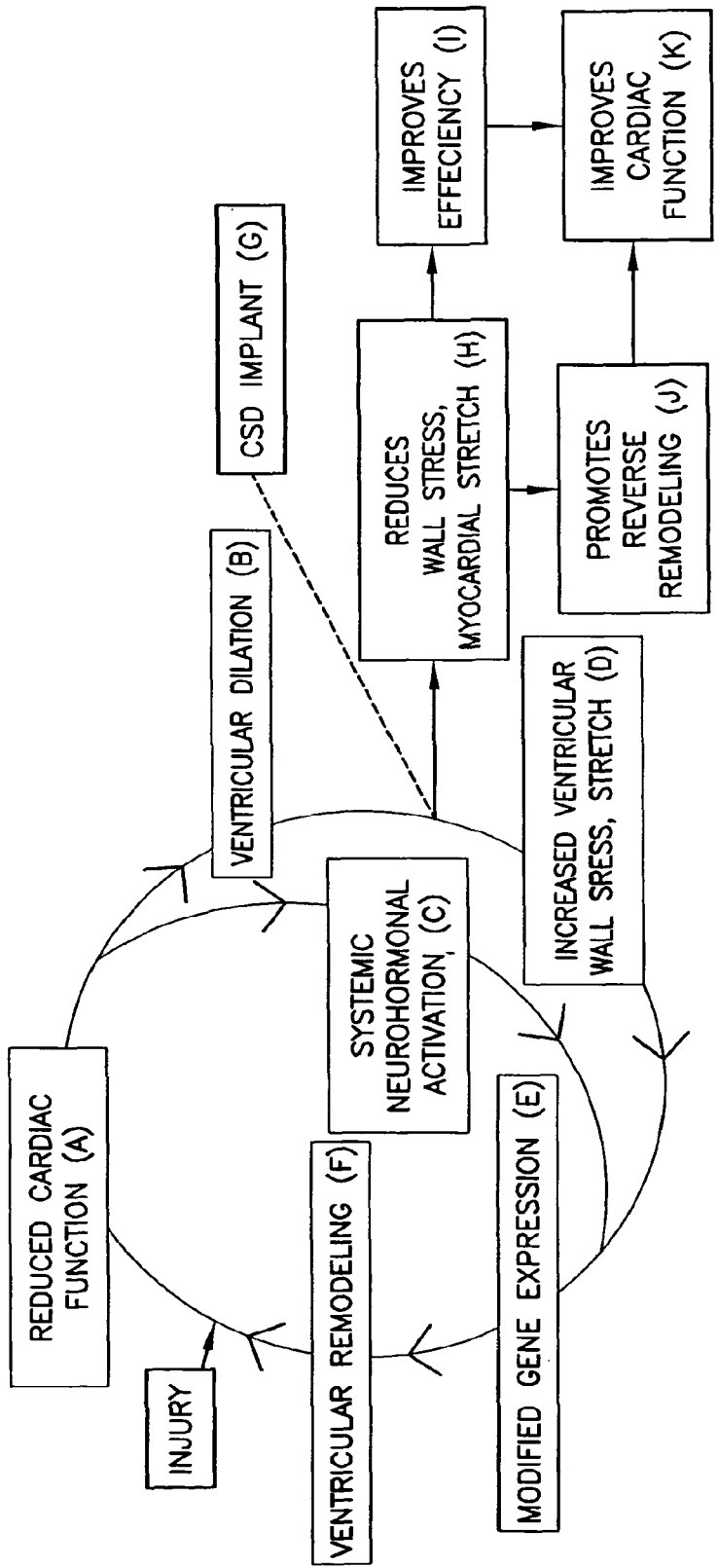
FIG. 3 is a schematic showing the theory of operation of a cardiac support device.

It is believed that the cardiac support device stimulates a physiological response due to a mechanical effect, a tissue-material interaction, or some combination thereof. While the physiological response can be difficult to predict, the mechanical interactions are more straightforward. FIG. 3 is a schematic showing how a cardiac support device interrupts the cycle of heart failure by disrupting excessive ventricular dilatation (i.e., abnormal dilation) during diastolic filling. Briefly, following an injury to the myocardium, the heart's function may be reduced (A). This stimulates a compensatory response of ventricular dilatation (B) to improve output. However, ventricular dilatation causes increased wall stress and stretch (D), which then triggers neurohormonal activation (C), leading to modified gene expression (E) which in turn leads to structural and functional changes in the myocardium. These changes are also referred to as ventricular remodeling (F). This further reduces cardiac function causing the cycle to repeat with additional compensatory dilatation. FIG. 3 illustrates the potential benefits of a cardiac support device providing wall support and resistance to ventricular dilatation. A cardiac support device reduces the myocardial wall stress and stretch (H), which helps to break the heart failure cycle and leads to improved efficiency (I), reverse remodeling (J) and ultimately improved cardiac function (K).

Figure 15:
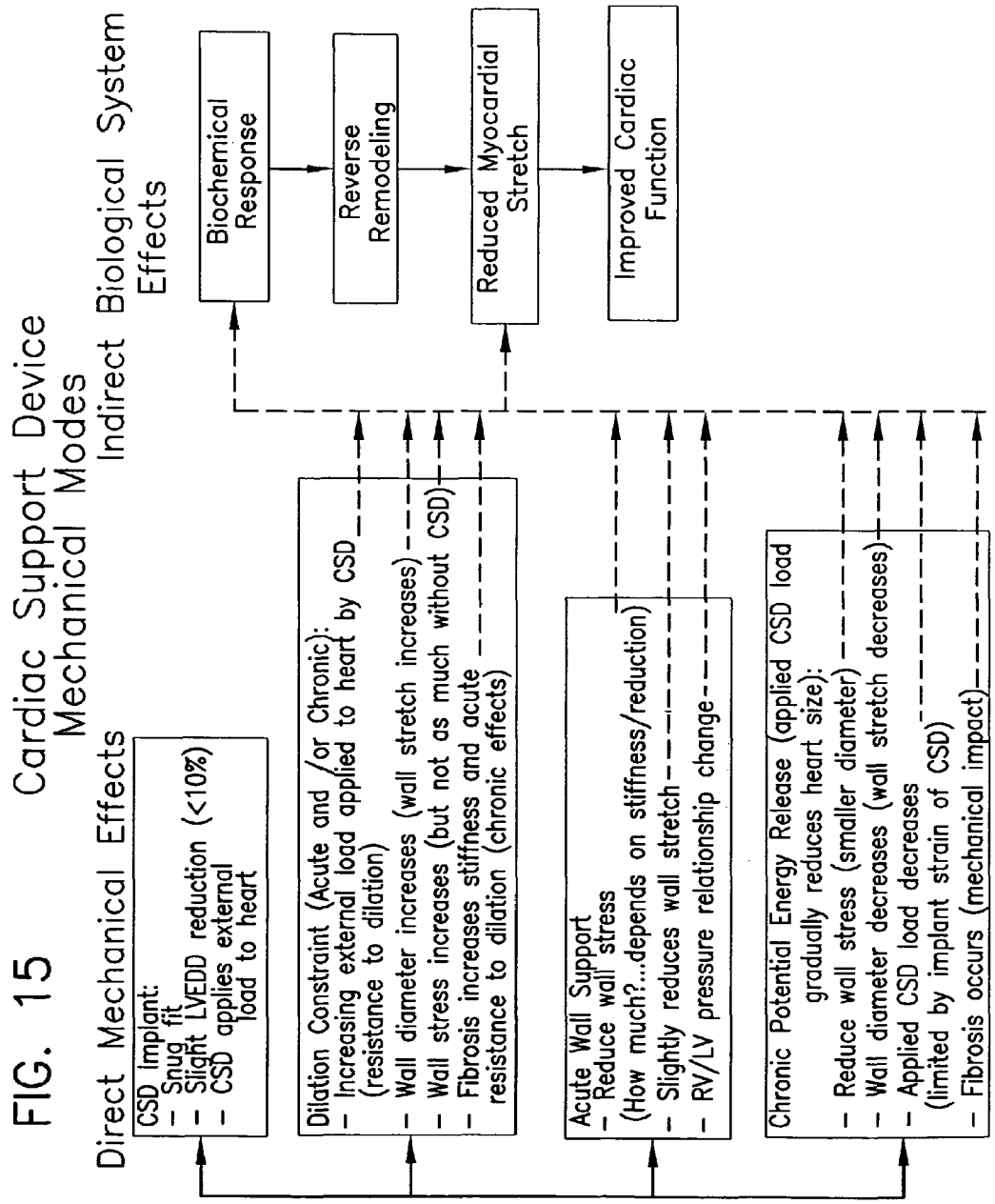
FIG. 15 is a schematic of the mechanical roles in cardiac support device therapy.

The mechanical effects that help interrupt the ongoing ventricular dilatation in the heart failure cycle can be divided into at least three mechanisms or components: (1) dilatation constraint (acute and/or chronic); (2) acute wall support; and (3) chronic potential energy release. As used herein, "dilatation constraint" means resisting expansion or dilatation of a heart that would result in a damaging increase in the volume of the heart. As used herein, "acute wall support" means reducing stress on the wall of the heart or supporting the internal pressure (i.e. reducing transmural wall pressure) of the heart by off-loading the heart acutely, at the time of the device implant. As used herein, "chronic potential energy release" refers to the potential energy of the device that is available (and released) to encourage reduction in the size of the heart, in terms of volume and/or dimension over time following implant of the device. Many of the device parameters, whether used for dilatation constraint, acute wall support and/or potential energy release, overlap. However, for the sake of clarity the design characteristics and/or the method for implanting a device for each of the three mechanisms or components will be discussed separately below. FIG. 15 is a schematic diagram showing the mechanical modes for the device mechanisms and how they tie into the biological responses to support the theory of operation in FIG. 3.

1. Dilatation Constraint (Acute and/or Chronic)

Dilatation constraint refers to the resistance the device provides to short-term transient dilatation and/or chronic cardiac dilatation, in particular excessive ventricular dilatation. Generally, dilatation constraint does not require energy input into the device. The device is typically adjusted to conform to the epicardial surface, to resist further dilatation of the heart. "Acute" dilatation constraint refers to resistance to cardiac dilatation from short term loading such as exercise loading. Exercise loading refers to the loading that occurs when a person performs a physical activity such as exercise. In exercise loading, the heart increases it's volume to provide more output using the Frank-Starling relationship. However, the increased volume results in increased end diastolic loading of the ventricular wall due to the Law of LaPlace. The Law of LaPlace is based on the concept that the larger the vessel radius, the larger the wall tension required to withstand a given internal fluid pressure. Larger ventricular chamber volumes generally correspond to larger chamber radii. "Chronic" dilatation constraint refers to resistance to continued dilatation due to prolonged volume loading and cardiac remodeling. Increased volume loading can also result from the intake of fluids, which is not discussed here, or kidney damage that is also associated with heart disease.

During dilatation constraint, the device reduces the ventricular wall stress and stretch increase that accompany acute and continued dilatation in heart failure. Both the reduction in ventricular wall stress and stretch increase are "myocardial displacement dependent." As used herein, the phrase "myocardial displacement dependent" means that the amount of support or loading provided by the cardiac support device is dependent on the amount of myocardial wall dimensional dilatation caused by disease progression or excessive loading. For this mechanical component, the compliance of the device can be an important characteristic. Generally, the compliance of the device can be important for acute loading before the fibrosis encapsulates the device and for long-term chronic dilatation. However, device compliance tends to be less important for acute loading after the fibrosis develops. Generally, lower compliance (i.e. higher stiffness) tends to provide more resistance and support for dilatation.

Generally, support devices such as those mentioned in the Background section of this application, have focused on the mechanism of dilatation constraint.

Figure 4A:
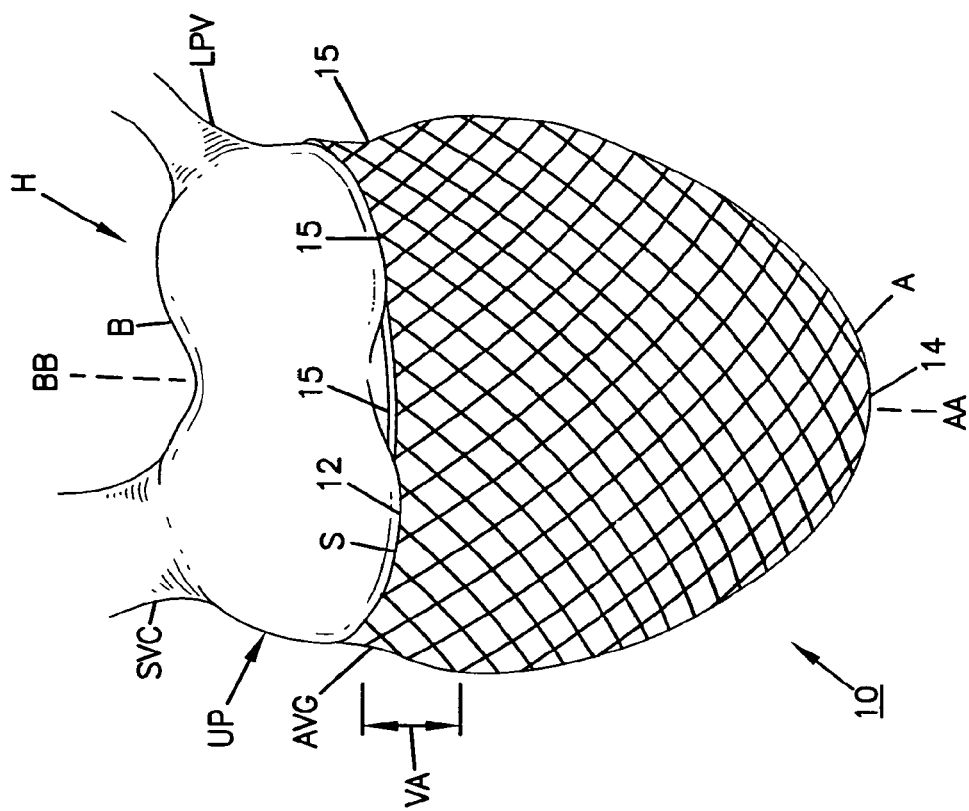
FIG. 4A is a side elevation view of a diseased heart in diastole with the device of FIG. 4 in place.
Figure 4:
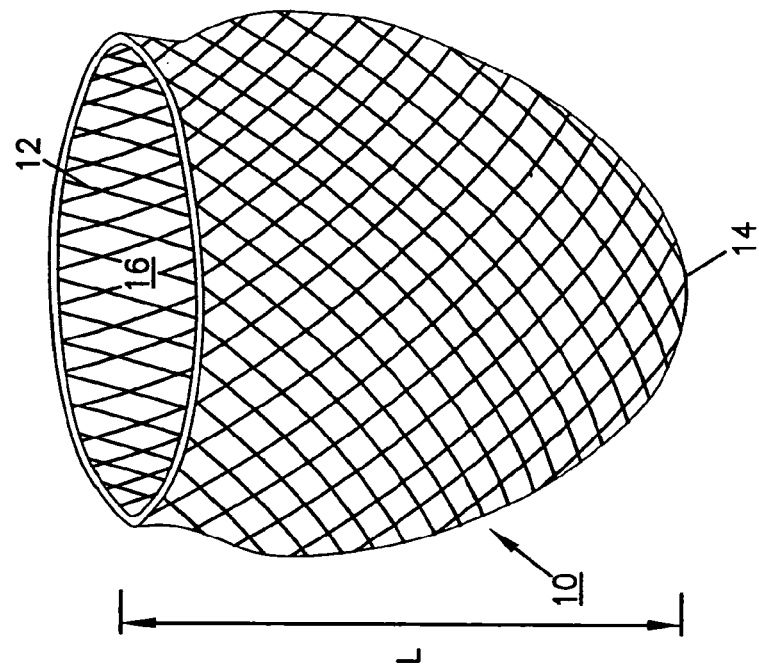
FIG. 4 is a perspective view of an embodiment of a cardiac support device according to the present invention.

Generally, when the device is used for dilatation constraint, the device 10 surrounds the myocardium MYO, as shown, for example, in FIG. 4. As used herein, "surround" means that the device provides reduced expansion of the heart wall during diastole by applying constraining surfaces at least at diametrically opposing aspects of the heart. Generally, the diametrically opposed surfaces are interconnected, for example, by a continuous material that can substantially encircle the external surface of the heart.

In one embodiment, the device is configured as a jacket 10 that defines a volume 16. Preferably the volume 16 is substantially the same size as or larger than the volume of the heart H, in particular the lower portion LP of the heart, at the completion of systolic contraction such that the jacket 10 exerts no or only a slight pressure on the heart at end systole. Generally, the jacket 10 is adjusted such that the jacket 10 resists enlargement of the heart H during diastole without significantly assisting contraction during systole. At time of placement, the device preferably exerts no or only a small pressure on the heart H at end diastole of less than 10 mm Hg, more preferably less than or equal to 5 mm Hg, most preferably less than or equal to 2 mm Hg. Such pressure may be determined by comparing load to the right ventricular end diastolic pressure.

Figure 8:
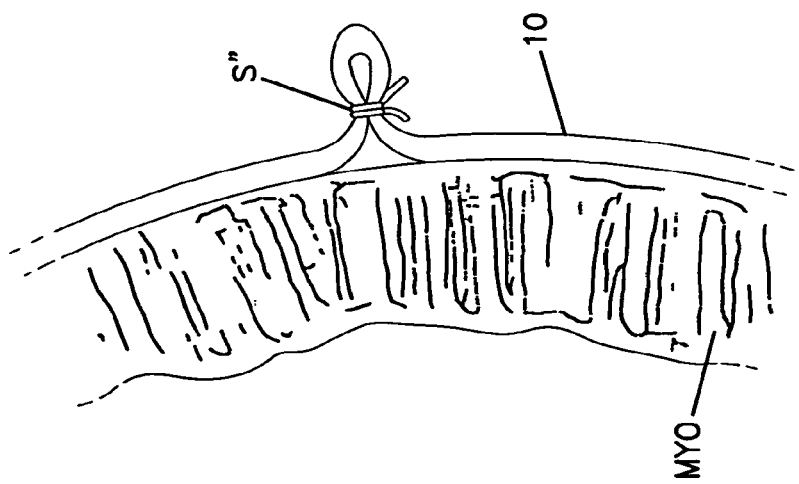
FIG. 8 is a cross-sectional view of a device of the present invention overlying a myocardium and with the material of the device gathered for a snug fit.

To permit the jacket 10 to be easily placed on the heart H, the volume and shape of the jacket 10 may be larger than the lower portion LP during diastole. So sized, the jacket 10 may be easily slipped around the heart H. Once placed, the jacket's volume and shape can be adjusted for the jacket 10 to snugly conform to the external geometry of the heart H during diastole. For example, excess material of the jacket 10 can be gathered and sutured S" (FIG. 8) to reduce the volume of the jacket 10 and conform the jacket 10 to the shape of the heart H during diastole. This shape represents an adjusted volume. The jacket 10 resists enlargement of the heart H-beyond the adjusted volume without interfering with contraction of the heart H during systole. As an alternative to the gathering shown in FIG. 8, the jacket 10 can be provided with other ways of adjusting volume. For example, as disclosed in U.S. Pat. No. 5,702,343, the jacket can be provided with a slot. The edges of the slot can be drawn together to reduce the volume of the jacket. The volume of the jacket can be adjusted prior to, during, or after application of the device to the heart.

Although, for dilatation constraint, the device is generally adjusted to a snug fit as described above, it is also possible to obtain the benefits of dilatation constraint using a device that defines a volume that is smaller than the volume of the portion of the heart H on which it is to be placed at end diastole. In this embodiment, the device is stretched in order to place it around the heart H, such that the compliance of the jacket 10 material and the amount of expansion of the material at end diastole determine the fit of the device without any further adjustment.

2. Acute Wall Support

Acute wall support refers to a more immediate effect of the cardiac support device. Generally, acute wall support is obtained by adjusting the device such that the device applies an external pressure to the heart. If desired, the device can be adjusted to provide a dimensional reduction in the heart size. For example, the device may be adjusted to slightly reduce cardiac dimension at the time of implantation, preferably, no more than 10% reduction in internal Left Ventricular End Diastolic Dimension (LVEDD). Thus rather than just reducing the increase in wall stress and stretch due to dilatation constraint, energy is actively input at the time of implantation to reduce the load on the wall acutely. However, after the device is placed on the heart, no further external energy is added. Thus, the device is still considered a "passive" device. Acute wall support reduces wall stress (load dependent) and reduces wall stretch (myocardial displacement dependent). As used herein, the phrase "load dependent" means that the reduction in wall stress is dependent on the amount of load applied, independent of the amount of dimensional change. The reduction in end diastolic wall stress is based on the change in transmural heart wall pressure. In contrast, the amount of reduced wall stretch is related to the dimensional reduction in the heart size. In contrast to a dilatation constraint mechanism, energy is input at the time of implantation for acute wall support and the material compliance is less important. However, as mentioned previously, these components overlap such that the benefits from both dilatation constraint and acute wall support can be realized from the same device.

Figure 7:
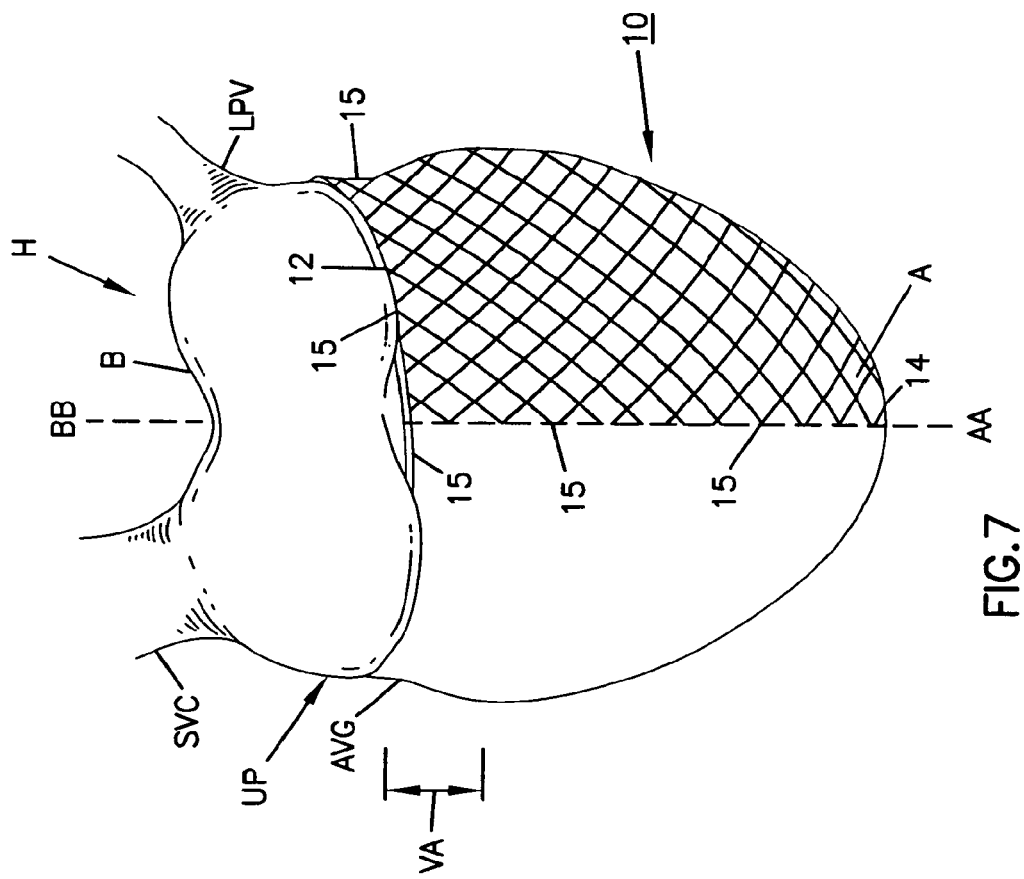
FIG. 7 is a side elevation view of a diseased heart in diastole with another embodiment of a cardiac support device in place.

If the device is configured as a jacket 10, it may be desirable to have a volume and shape that is larger than the lower portion LP during diastole so that the jacket 10 may be easily slipped around the heart H and adjusted (as with dilatation constraint). However, it may also be desirable to use a device with a volume and shape that is smaller than the lower portion LP of the heart H during diastole. In this embodiment, the compliance of the jacket 10 and expansion at diastole determine the fit, without additional adjustment. When selecting or adjusting the jacket 10 for acute wall support, care should be taken to avoid impairing normal cardiac function. During diastole, the left ventricle LV fills with blood. If the jacket 10 is too tight, the left ventricle LV may not adequately expand and left ventricular filling pressure may rise. Furthermore, if the device encloses both ventricles such as in FIG. 4A, care should be taken when selecting or adjusting the jacket 10, because the wall of the right ventricle RV tends to be thinner than the wall of the left ventricle LV and the pressure in the right ventricle RV tends to be lower than the pressure in the left ventricle LV. Preferably the pressure exerted by the jacket 10 on the heart H at end diastole is not greater than the end diastolic pressure of the right ventricle RV. If the pressure exerted by the jacket 10 is greater than the pressure of the right ventricle RV, expansion and/or filling of the right ventricle RV may be compromised. However, for a device that is applied to only one of the ventricular chambers such as the Left Ventricle LV as shown in FIG. 7, the pressure exerted by the jacket 10 at end diastole is preferably less than the end diastolic pressure of the LV.

Generally a jacket 10 that imposes between about a 5% to about a 10% reduction in LVEDD (left ventricle end diastolic dimension) serves to reduce cardiac volume without compromising cardiac function. Preferably, the jacket 10 exerts pressure at end diastole between about 2 mm Hg and about 20 mm Hg, more preferably between about 5 mm Hg and about 15 mm Hg, and most preferably between about 5 mm Hg and about 10 mm Hg, depending on the internal end diastolic pressures of the heart chambers. The jacket may be designed with multiple sections with different compliances and pressures for a specific heart chamber.

3. Chronic Potential Energy Release

Figure 6:
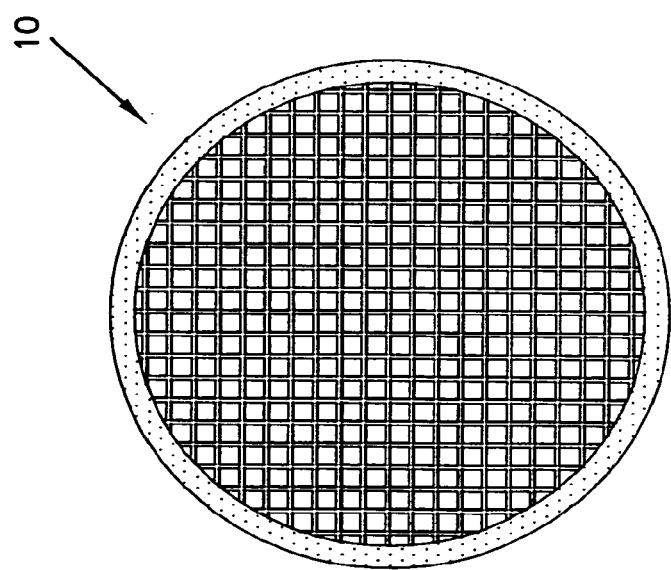
FIG. 6 is a plan view of an alternate embodiment of a cardiac support device.

In addition to dilatation constraint and acute wall support, the cardiac support device may also be able to use stored potential energy to enhance heart size reduction over time. Based on the Law of LaPlace, reduced heart size will reduce the myocardial wall load for a given internal chamber pressure. The chronic potential energy release mechanism and the device properties that enable the size reduction are key aspects of this invention. Generally, the potential energy of the device is due to the fabric being stretched at the time of implantation. Typically, the device is selected and/or adjusted (if necessary) to have a "resting" size and/or volume that are smaller than that of the enlarged heart to which it is applied. Preferably the "resting" size of the device is approximately the same size as the heart in a healthy state or some other desired target size. As used herein the term "resting" means that the fibers of the fabric are in a relaxed state such that energy is not required to keep the fibers in the "resting" or "relaxed" state. When the material is "stretched" to accommodate the enlarged heart, work energy must be input to create the "stretched" configuration. The amount of energy input and stored in the device is based on the amount of strain (or stretch) and the load required to obtain that strain. According to one aspect of the invention, the material is stretched during implantation, wherein the stretching provides the material with potential energy that can be used to enhance reduction in the size of the heart. In one embodiment, the material is stretched to provide a stretched volume that is at least 20% greater than the resting volume, more preferably, the material is stretched to provide a stretched volume that is about 40% greater than the resting volume, more preferably about 60% greater than the resting volume. The maximum stretch should be based on the limit of heart volume reduction desired. Similarly, a patch device that covers a small area (i.e. FIG. 6) rather than encapsulating a volume may have similar stretch targets based on area or length rather than volume.

Again as with acute wall support care should be taken to avoid exerting too much pressure on the heart, such that cardiac function is impaired. For this mechanical mechanism or component, the device preferably exerts pressures similar to those described for the acute wall support mechanism. Lower pressures may be effective and more preferred depending on the compliance and elasticity of the device and the desired level of stored potential energy.

Both the compliance and elasticity of the material are important parameters for the chronic potential energy release mechanism. Compliance refers to the ability of the device to deform under load. In engineering terms it is the inverse of stiffness. Elasticity refers to the ability of the device to return to its original dimension upon unloading after being deformed by a load. The compliance of the device and the load applied determine the amount of energy added to the system at the time of implant. However, the device elasticity determines the new resting state of the device after it has been stretched out for implantation, and how much stored potential energy can be released from unloading the device. Once the device is implanted, the heart will generally reduce in size over time to reduce the external load applied by the device. The amount of potential energy stored and the elasticity in the device will affect how much the device can mechanically reduce and reshape the heart from a dilated size to possibly a normal size. A device having high compliance and high elasticity is generally preferred for this mechanism to increase the amount of potential energy that can be stored and recaptured.

It is noted that the tissue response to the implanted device may cause the device to be encapsulated in a thin layer of fibrosis. The collagenous fibrotic tissue can be remodeled when it is subjected to chronic loads. Thus, after the device is encapsulated by fibrosis, the composite compliance of the fibrosis and device may be reduced for short-term transient loads. However, for long-term loads such as reduction in the heart size due to the chronic potential energy release of the device, fibrosis is believed to have only a minor or insignificant impact on the compliance and elasticity of the device. Over time the fibrosis is unlikely able to support the load from the heart or the device. Thus, the fibrosis tends to remodel as the heart reduces over time and the compliance and elasticity of the device continue to drive the mechanical reduction in heart size until the potential energy of the device is fully released or the heart size stabilizes.

Figure 16:
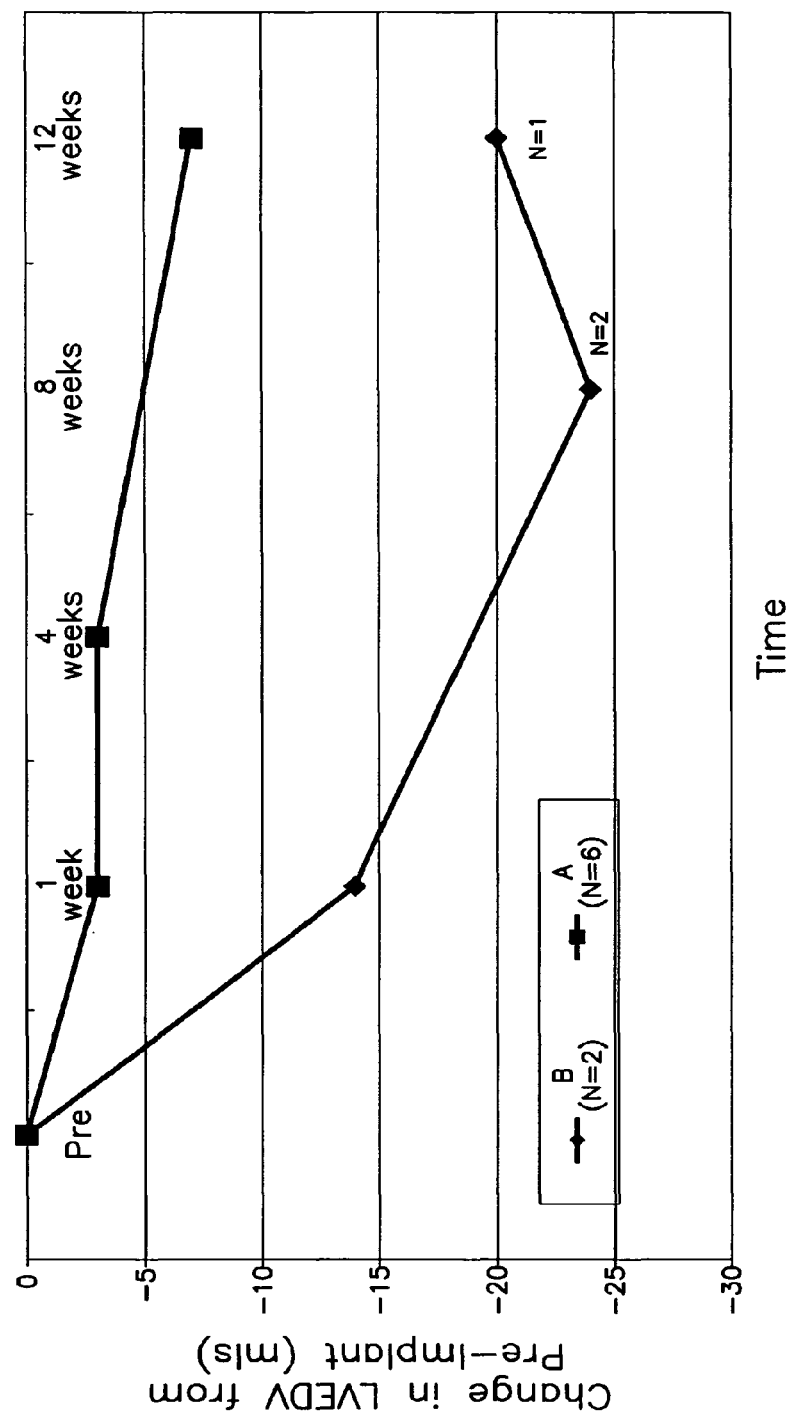
FIG. 16 is a plot of LVEDV (left ventricular end diastolic volume) change results from a pre-clinical animal study with a horizontal axis depicting time and with a vertical axis depicting change in LVEDV from pre-implant conditions.

The chronic potential energy release mechanism of the device reduces wall stress and reduces wall stretch, both of which are myocardial displacement dependent. As the device mechanically causes the heart to reduce in size, the heart wall stress and stretch reduce due to the change in geometry. The chronic potential energy mechanism was demonstrated in a pre-clinical animal model. FIG. 16 with the early results of an animal study using canines with failing hearts shows significantly larger left ventricular end diastolic volume (LVEDV) reduction in two animals implanted with a higher compliance device (A) when compared to six animals implanted with the current lower compliant device (B). All animals were implanted with similar loading and little to no acute reduction at the time of implant. The additional potential energy stored in the high compliance devices was able drive the size reductions by over 3 times more volume.

C. Cardiac Support Device.

The invention provides a device having a compliance and/or elasticity to render it suitable for use for one or more of the following treatments: resisting enlargement of the cardiac dimension (dilatation constraint), offloading stress from the myocardial wall (acute wall support), and enhancing reduction in cardiac dimension (chronic potential energy release).

Generally, the device is configured to cover at least part of the epicardial surface, typically at least the ventricles. As used herein, the term "cover" means that the device is in contact with an external surface and applies a force on the surface of the heart. Generally, the device contacts an epicardial surface of the heart, but it can also be applied over the pericardium.

A device that "covers" the lower extremities of the heart may be constructed as a continuous material that can substantially encircle, or "surround", the external surface of the lower extremities of the heart (See, FIGS. 4, 4A, 5, 5A). In an alternate embodiment, the device provides for localized support of the heart, particularly during diastole. According to this embodiment, a device 10 may be configured as a "patch" (See, FIG. 6). A patch may be useful to provide dilatation constraint or acute wall support over a localized area of injury such as an acute myocardial infarction (AMI) or a wall aneurysm. In the case of an aneurysm, it may be advantageous to take advantage of the chronic potential energy release mechanism to restore the wall shape over time. When discussing a "patch", the size of the patch is selected to cover an area of the epicardial surface of the heart without completely surrounding the circumference of the heart. In yet another embodiment, the device may be configured to cover only a left or right ventricle (See, FIG. 7). Typically, in this embodiment, the device is attached to the heart proximate the septal wall S'. If desired, the device can be constructed from material having one or more compliances or be constructed as one or more separate components. The mechanical characteristics of each component may be designed to specifically target one or more of the mechanical mechanisms of device therapy previously described. With reference now to FIGS. 4, 4A, 5 and 5A, the device of the present invention is shown as a jacket 10 of flexible, biologically compatible material. As used herein, the term "biologically compatible material" refers to material that is biologically inert such that the material does not adversely result in excessive injurious responses such as chronic inflammation which would adversely affect the myocardium and potentially surrounding tissues.

Figure 5A:
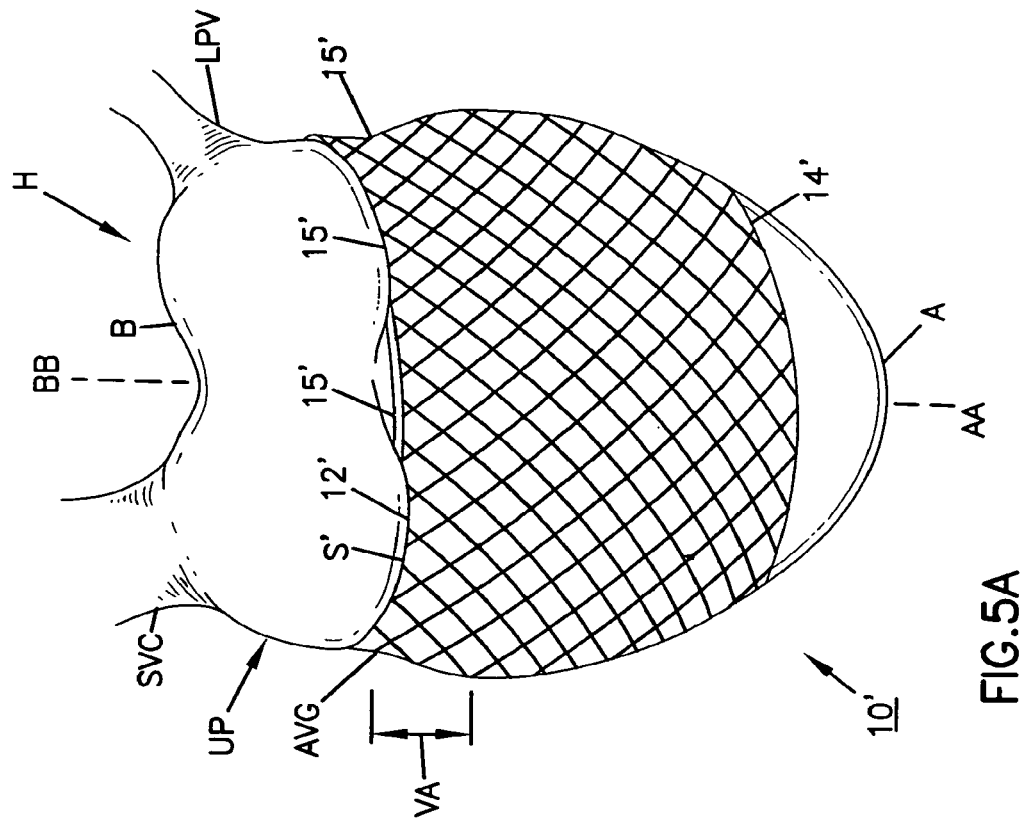
FIG. 5A is a side elevation view of a diseased heart in diastole with the device of FIG. 5 in place.
Figure 5:
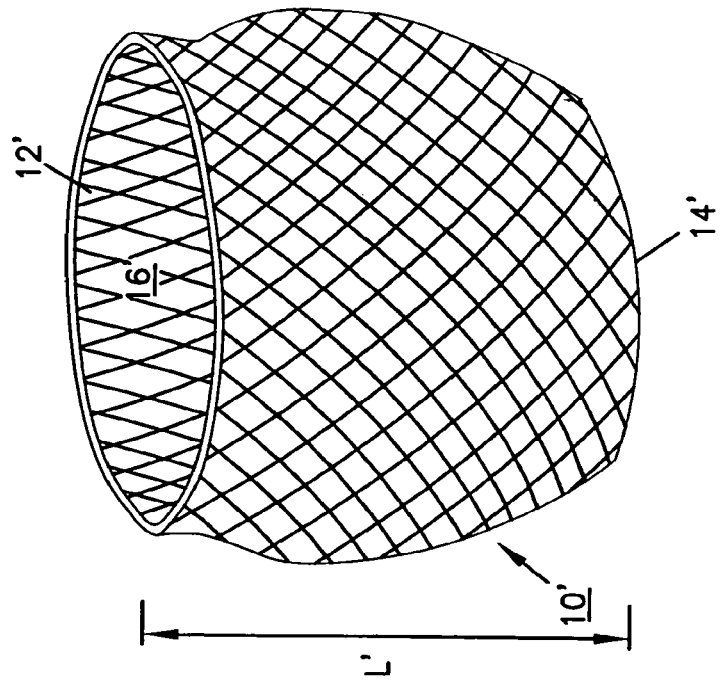
FIG. 5 is a perspective view of another embodiment of a cardiac support device with the apex open according to the present invention.

A jacket 10 is an enclosed material having upper and lower ends 12, 14. The jacket 10, 10' defines an internal volume 16, 16' which is completely enclosed but for the open ends 12, 12' and 14'. In the embodiment of FIG. 4, lower end 14 is closed. In the embodiment of FIG. 5, lower end 14' is open. In both embodiments, upper ends 12, 12' are open. Throughout this description, the embodiment of FIG. 4 will be discussed. Elements in common between the embodiments of FIGS. 4 and 5 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be enclosed within the volume 16. The jacket 10 can be slipped around the heart H. The jacket 10 has a length L between the upper and lower ends 12, 14 sufficient for the jacket 10 to enclose the lower portion LP. In one embodiment, the upper end 12 of the jacket 10 extends at least to the valvular annulus VA and further extends to the lower portion LP to enclose at least the lower ventricular extremities LE. If desired, the jacket 10 may be sized so that the upper end 12 resides in the A-V groove AVG. Where it is desired to treat the upper portion UP, the jacket 10 may be extended to cover the upper portion UP.

After the jacket 10 is positioned on the heart H as described above, the jacket 10 is secured to the heart. Preferably the jacket 10 is secured to the heart H through sutures. The jacket 10 is sutured to the heart H at suture locations 15 circumferentially spaced along the upper end 12. While a surgeon may elect to add additional suture locations to prevent shifting of the jacket 10 after placement, the number of such locations 15 is preferably limited so that the jacket 10 does not restrict contraction of the heart H during systole. Other attachment methods such as staples or clips may be acceptable as an alternative to sutures along the upper end 12.

The jacket 10 can be adjusted to provide the appropriate fit after placement around the heart. Alternatively, the jacket 10 can be sized to obtain the appropriate fit based on device compliance, desired level of fit and the size of the portion of the heart H the device is intended to cover.

a. Compliance

As used herein, the term "compliance" refers to the load required to deform the material. As mentioned previously, in the field of engineering it is the inverse of stiffness. The compliance can be described in terms of displacement (inches or centimeters), strain (inch/inch or cm/cm) or volume (in.sup.3, cm.sup.3 or ml) per a unit load (pounds or kilograms) or pressure (psi or mm Hg). The compliance of the cardiac support device can have a significant impact on the mechanical mechanism and effectiveness in the therapy, as well as allowing it to be stretched for accommodating an enlarged heart. It should also be noted that compliance is not necessarily constant over a given range of displacement. In fact, compliance that decreases with increased stretch is a common characteristic of many materials.

Due to the Frank-Starling behavior of the heart, a cardiac support device that has less compliance than the myocardium at small deformations may not be desirable. Generally, the cardiac output demand for the heart changes depending on physical activity. To increase the cardiac output according to the Frank-Starling mechanism, the pre-load or end diastolic volume of the heart is increased such that the muscle fibers are temporarily stretched. The stretching of the muscle fibers helps increase heart capacity and myocyte contractility and therefore cardiac output. If a cardiac support device with less compliance than the myocardium is applied to the surface of the heart, the heart may not be able to utilize the Frank-Starling mechanism effectively without increasing ventricular filling pressure. Thus, ventricular filling may be negatively impacted and mimic a cardiovascular disease known as constrictive pathologies. Thus, a cardiac support device with a higher compliance than the myocardium is generally preferred.

Other evidence indicating that cardiac support with higher compliance may be preferable can be found in examining the compliance of the normal pericardium and the latissimus dorsi muscle used to wrap the heart for cardiomyoplasty. The stiffness of living myocardium and latissimus dorsi muscle is complex and has both active and passive elements. For simplicity, only the passive elements will be examined.

Table 1 contains a comparison of passive stiffness of myocardial tissue, pericardial tissue, latissimus dorsi muscle tissue and a sample cardiac support device that has been described in previous patents (i.e. U.S. Pat. No. 6,085,754 and International patent application publication No. PCT WO 01/95830) (this sample cardiac support device is referred to herein as the "prior knit device"). The values in Table 1 were derived based on uniaxial loads at strains less than 30%. As shown in Table 1, the pericardial tissue is much more compliant than the myocardium for low strains, but stiffens at higher strains to become less compliant than the myocardium. If the pericardium was as stiff for low strains as higher strains, ventricular filling would probably be impaired, similar to constrictive pericarditis or cardiac tamponade. The stiffness comparisons provided in Table 1 illustrate that the latissimus dorsi (sometimes used to wrap the heart for cardiomyoplasty) is also more compliant than the myocardial tissue. The sample cardiac support device (i.e., the prior knit device) also has a greater compliance than the myocardium and similar, but slightly less compliance than the latissimus dorsi muscle. As mentioned earlier in the Background section, Oh et al. used a very non-expansible material to wrap around the heart known as Bard Marlex. Although the Bard Marlex helped to limit progressive dilatation in this study, it was not as effective as the latissimus dorsi muscle in adynamic cardiomyoplasty. The uniaxial stiffness of Bard Marlex has been measured to be less compliant than the myocardium as shown in Table 1. The data in Table 1 thus supports the concept that a myocardial support device should preferably be more compliant than the myocardium.

TABLE 1

| Component | Relative (uniaxial) Stiffness* (lbs/in) | References |
|---|---|---|
| Myocardium | 3.8 to 5.0 | Sideman & Beyar, "Simulation and Control of the Cardiac System," CRC Press, Inc., 1987, Chapter 5. |
| Normal Human Pericardium | 0.1 to 25.0 | Lee et al., "Biaxial mechanical properties of human pericardium and canine comparisons," Am. J. Physiol, 1987, 253: H75-H82. |

TABLE 1-continued

| Component | Relative (uniaxial) Stiffness* (lbs/in) | References |
| --- | --- | --- |
| Latissimus Dorsi | 0.5 to 0.7 | Reichenbach et al., "Passive characteristics of conditioned skeletal muscle for ventricular assistance," ASAIO J., 1999 July-August; 45(4): 344-9. |
| Cardiac Support Device (i.e., the prior knit device) | 0.8 to 1.7 | Bench testing |
| Bard Marlex | 5.9 to 25.0 | Bench testing |

*Notes:
Slope of stress versus strain curve (i.e. σ/ε) is a measure of stiffness (lbs/in.sup.2).
Incorporating the material thickness (t), a measure of relative stiffness is given by σt/ε (lbs/in).
This is a measure of load per inch width of material required to produce a given strain.
Compliance is the inverse of stiffness.
The uniaxial stiffness for various materials were derived from references listed for strains up to 30%.

In the Kass et al. article mentioned in the Background section, it was speculated that an artificial elastic "sock" could be used to replace the latissimus dorsi muscle in adynamic cardiomyoplasty. This reference seems to use the term elastic relative to compliance (not in it's true engineering sense) and makes the comparison to replacing the latissimus dorsi with a device of similar compliance. The cardiac support device in Table 1 has compliance that is comparable or slightly less than the latissimus dorsi muscle. However, the inventors have found that a high compliance cardiac support device may have superior performance. The advantages of a high compliance cardiac support device (i.e., a device having a compliance greater than the latissimus dorsi) are not disclosed by Kass et al.

Compliance of cardiac support devices can be measured in vitro to determine either uniaxial directional compliance or 3-dimensional full device volumetric compliance. The uniaxial directional compliance can be determined by taking samples of a selected device. These samples can be mounted on a standard hydraulically actuated tensile testing machine such as those supplied by MTS Systems Corporation or Instron Corporation. The compliance or stiffness characteristics of the device are obtained by measuring the load versus deflection of the sample. The device and Bard Marlex stiffness provided in Table 1 were determined using this method for comparison purposes.

In use, the compliance of the cardiac support device is more realistically based on 3-dimensional loading than uniaxial loading. Thus, an in vitro test was developed to examine full device compliance. For this test, the circumference of the base end of a sample cardiac support device (i.e., the prior knit device) was mounted to a support plate to simulate the attachment of a device near the heart valve plane. A balloon bladder was placed in the volume defined by the device and filled with saline to simulate the external heart ventricular volume. To offset the effect of the weight of fluid within the balloon, the mounted device and balloon are suspended in a tank of saline maintained at approximately 37.degree. C. The apex of the device is supported so when the fluid is added to the balloon, the device expands primarily circumferentially, to better simulate the dilatation of a heart in failure. The internal volume of the balloon was monitored by recording the volume of fluid that was added incrementally. At each fluid increment the pressures within the balloon are monitored using a Millar catheter tip transducer and between the device and the external surface of the balloon using a "pillow" device and methods similar to those described by Tyberg et al. ("Static and dynamic operating characteristics of a pericardial balloon," Hamilton D R, Devries G, Tyberg J, J Appl Physiol, 2001 April; 90(4):1481-1488). Both the internal balloon pressure and pillow pressures track very closely, indicating very little resistance from the balloon.

Figure 10:
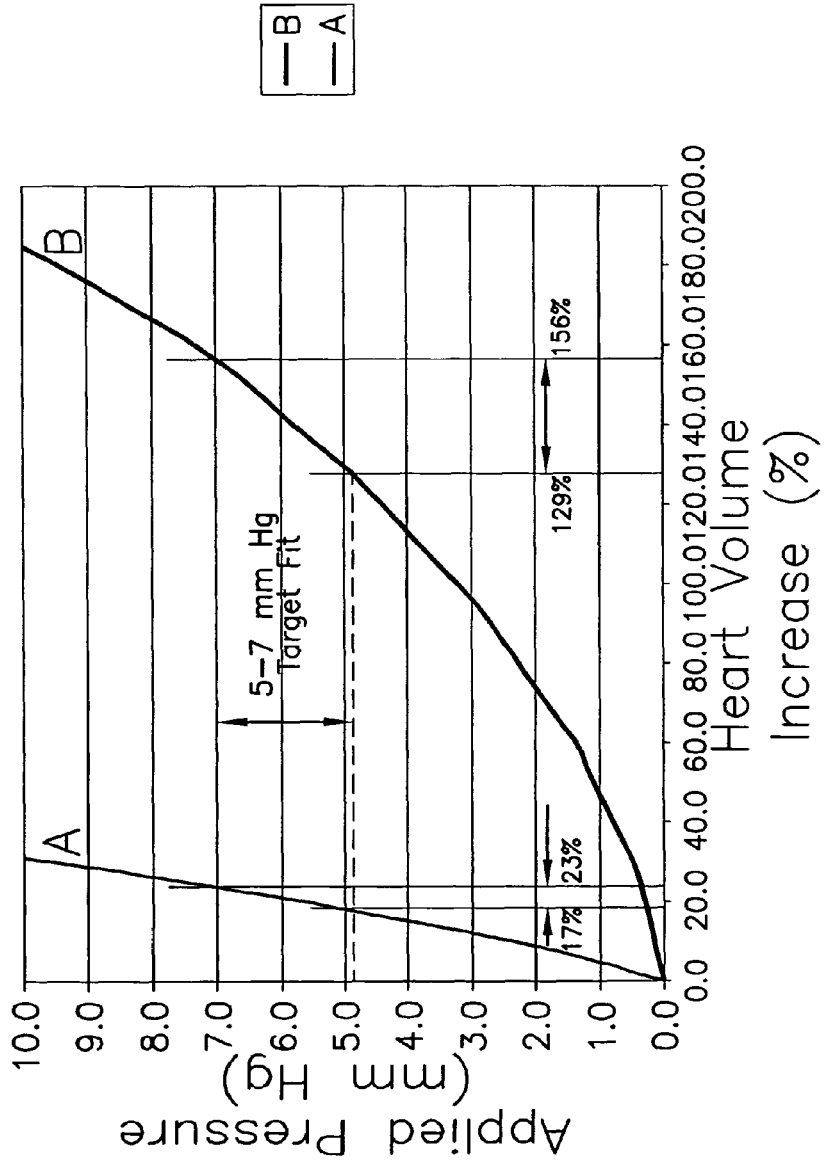
FIG. 10 shows compliance curves (pressure versus % volume change) for a lower compliance (A) and a higher compliance (B) device.

Typical compliance curves obtained using this method with normalized percentage volume changes are shown in FIG. 10. FIG. 10 illustrates the 3-dimensional or volumetric compliance curves for two cardiac support device configurations. Curve A illustrates a lower compliance device, while curve B represents a higher compliance device.

Data indicates that a high compliance cardiac support device may be desirable in many circumstances. As discussed above, the compliance of a cardiac support device can vary over a given range of displacement, or depending whether or not the device is subject to uniaxial or multiaxial loads.

As used herein, the term "high compliance cardiac support device" refers to a device having a compliance that is greater than that of a normal myocardium, and more preferably greater than the compliance of the latissimus dorsi muscle. In one embodiment, or characterization, the high compliance device of the invention can thus be described as having a stiffness less than 3.8 lbs/in for uniaxial strains up to 30%. As shown by the data in Table 1 and the discussions above, it may be more preferable that the device has a compliance that is greater than a normal Latissimus Dorsi muscle, i.e., a stiffness less than 0.5 lbs/in for uniaxial strains up to 30%. Typically, when referring to a "high compliance" device herein, the inventors are referring to a cardiac support device having a stiffness less than about 0.5 lbs/in when subjected to a uniaxial load at strains up to 30%, more typically between about 0.05 lbs/in and about 0.2 lbs/in. It will be appreciated that the foregoing description of data for strain up to 30% is intended to be representative and not to suggest strains greater than 30% are not applicable to the present invention.

Another way in which the compliance of the high compliance device can be characterized is based on 3-dimensional volumetric compliance in terms of the percentage of volume increase (%) over applied pressure (mm Hg). Using this characterization in a representative example, the high compliance device of the invention will have a compliance that allows at least a 3% increase in volume for every 1 mm Hg increase in pressure (3%/mm Hg), more preferably between about 5%/mm Hg and about 15%/mm Hg. Actual volumes will depend upon the specific compliance. Again, it will be appreciated the foregoing is a non-limiting example.

i. Material

Figure 9:
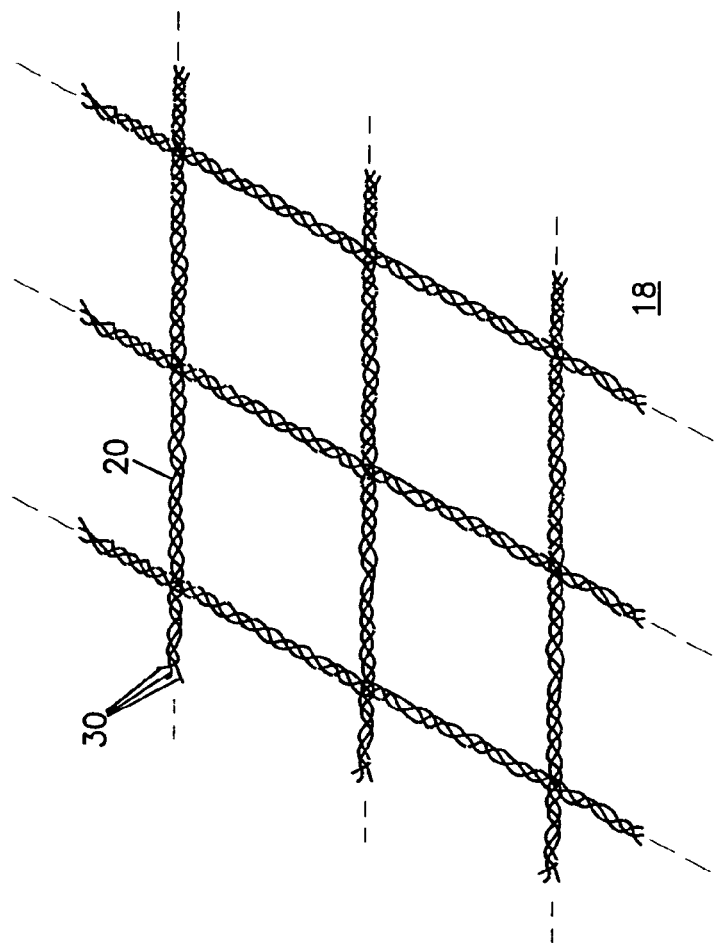
FIG. 9 is an enlarged simplified view of a the fabric of a knit construction at rest, suitable for use in the device of this invention.

The high compliance cardiac support device of the invention can be fabricated using various materials and configurations to provide the mechanical characteristics desired. In a preferred configuration, the device is constructed from a warp knitted fabric 18 of polyester fibers. Generally, the fabric 18 material is formed from intertwined fibers 20 that are made up of a plurality of filaments 30, as shown in FIG. 9. The compliance of the material may be due to a variety of factors, including, but not limited to, the compliance of the individual filaments 30 that make up the fibers 20 (see section b. Elasticity), the relative movement of the filaments 30 within a fiber 20, and/or the relative movement of the intertwined fibers 20 when subjected to load. Texturizing of the yarn can impact the compliance and elasticity of the fibers. Preferably, the fiber material and texturizing result in a compliant and elastic fiber such as a stretch polyester.

Compliance due to the relative movement (e.g., geometric deformation of the fabric openings) of the intertwined fibers 20 may be affected by the manner in which the fibers 20 are entwined. For example, a knit material will tend to be more compliant than a woven material because the loops of the knit are capable of deforming (e.g., widening or lengthening) to accommodate applied stress. In comparison, woven materials tend to have less elongation unless elastomeric fibers are used. Knit material also tends to recover well from deformation because the loops attempt to return to their original positions. The looped configuration of the fibers accommodates this recovery more readily than does the interwoven configuration found in woven materials. The ease and quickness with which elastic recovery takes place is also dependent on the fiber composition. The fibers 20 of the jacket 10 material may be entwined as a knit (for example, a warp knit) or as a weave. Preferably, the fibers 20 of the jacket 10 material are entwined as a knit.

ii. Manufacturing a High Compliance Device

The compliance of the cardiac support device can be due to the intertwining of the fabric fibers, or due to the compliance/elasticity of the fibers themselves, as discussed above. Additionally, the compliance of the cardiac support device can be altered by the method of processing the fabric.

For example, the compliance of the material of a cardiac support device can be increased by "shrinking" the material of the device, such that the device then includes more material within the same unit area and the fibers are closer together and more compressed, as compared to the device before the "shrinking" process. For example, shrinking can be accomplished by heating the device. A memory condition can be introduced by a high temperature exposure or set temperature within the fibers, which modifies the "resting" state of the fibers (i.e., the state to which they naturally return without the use of force). Exposure to temperatures below the set temperature can cause the fibers to respond by shrinking to the at rest condition. However, exposure to new temperature conditions above the original set temperature while subjected to a load will create a new at rest configuration. Additionally, changing the fabric knit configuration, fiber texturizing or fiber material can further increase the compliance of the original device.

Thus, in one embodiment, a high compliance device is manufactured by adding additional material to a fabric pattern of a lower compliance device (also referred to as the "original" device). Both patterns are shrunk to the same size, for example, using a heat set mandrel (i.e., the same heat set mandrel is used for the "original device" and the "highly compliant" device). This method can easily increase the compliance of the device 5 to 10 times (at low to moderate strains) over the original device.

In manufacturing, the device is shaped to that of a healthy heart so that the device not only uses its stored energy to reduce size but also to help the patient's heart restore shape. Both beneficial attributes are referred to as remodeling.

b. Elasticity

As used herein, the term "elastic" refers to the ability of the deformed material to return to its initial state after a deforming load is removed. A device that is highly elastic can undergo very large deformations, but upon unloading returns to or close to its original state. With respect to a cardiac support device, elasticity may be important to the cardiac support device for maintaining an external load on the heart as it reduces in size.

When a material is subjected to a deformation, the deformation is either plastic or elastic. If the deformation is plastic, it does not rebound when unloaded. The degree of elasticity for a given loading can be characterized as the percentage of the deformation that rebounds upon unloading. Thus when unloaded, an entirely elastic material would rebound to its original state and characterized as 100% elastic at that load. Whereas, a material that does not rebound at all from its deformed state would be considered to have undergone an entirely plastic deformation and would be considered elastic at that load. In general, the amount of elastic recovery for the cardiac support device (in %) can be calculated as 100% $(d_1-d_2)/d_1$, where $d_1$ is the initial deformation and $d_2$ is the deformation after unloading. The deformations $d_1$ and $d_2$ can be based on any dimensional measure of length, area or volume as long as the units are consistent.

Preferably the device 10 has an elastic recovery of at least about 50%. However, it should be at least enough to allow the device to deform elastically up to the desired reduction in cardiac dimension targeted for the chronic potential energy release. Thus, if the device is implanted at 50% fabric strain and the desired heart size is calculated to be at a point of 25% fabric strain, it would be preferable to have a device capable of at least about 50% elastic recovery, more preferably at least about 70% elastic recovery.

As with compliance, the elasticity of the material may be due to a variety of factors. The elasticity of the base material used to fabricate the device is one factor in determining the elastic recovery. For the cardiac support device, one suitable material is polyethylene terephthalate (PET), more commonly known as polyester. Other biologically compatible materials could also be used to provide the desirable amount of elasticity. In addition to the base material, the configuration and heat-induced memory are also important in determining the elasticity of the device. In one embodiment, a warp knitted fabric fabricated from continuous multi-filament set textured yarns is used. The fabric knit configuration contributes to the elastic performance of the device as well as its compliance. However, the process of texturizing the yarn fibers 20 introduces a permanent crimp in the yarn that is very important to the compliance and elastic performance of the final device.

The permanent crimp induced in the individual filaments 30 that make up the yarn fibers 20 during texturizing provides a memory to the yarn. The permanent crimp can be deformed when loaded, but will have a tendency to return to the crimped configuration when unloaded (i.e. elastically recover). The texturizing process generally involves heat and deformations to form the permanent crimp. Stretching the fabric and heating to a higher temperature during the final processing of the device can remove some of the yarn crimp and provide a new memory condition.

The preferred permanent yarn crimp for the original cardiac support device is produced by set texturizing the yarns, then processing the final device by heat setting it with the device slightly stretched. Increased compliance and elasticity can be obtained using the same polymer and fabric knit configuration, but with no final device heat set or by using other texturizing processes such as stretch textured yarns. As mentioned, in the preferred configuration elastic recovery is at least 50%, but most preferable 70% to 100%.

Device elasticity can be determined from the compliance curves for loading and unloading a device. The in vitro 3D balloon compliance test described in the previous section can be used to load and unload the device to determine the elastic rebound.

D. Benefits

The device 10 of the invention may provide some or all of the following benefits.

1. Reduction in Heart Dimension

The device 10 of the invention is a highly compliant and elastic device that is capable of mechanically reducing the heart size over time by using the chronic potential energy release mechanism previously described. The reduced heart size is beneficial due to reduced wall stresses, which may, in turn, lead to improved cardiac function. The benefit of reducing heart size with a high compliance device can be illustrated by comparing a lower compliant device to a high compliance device.

Figure 11:
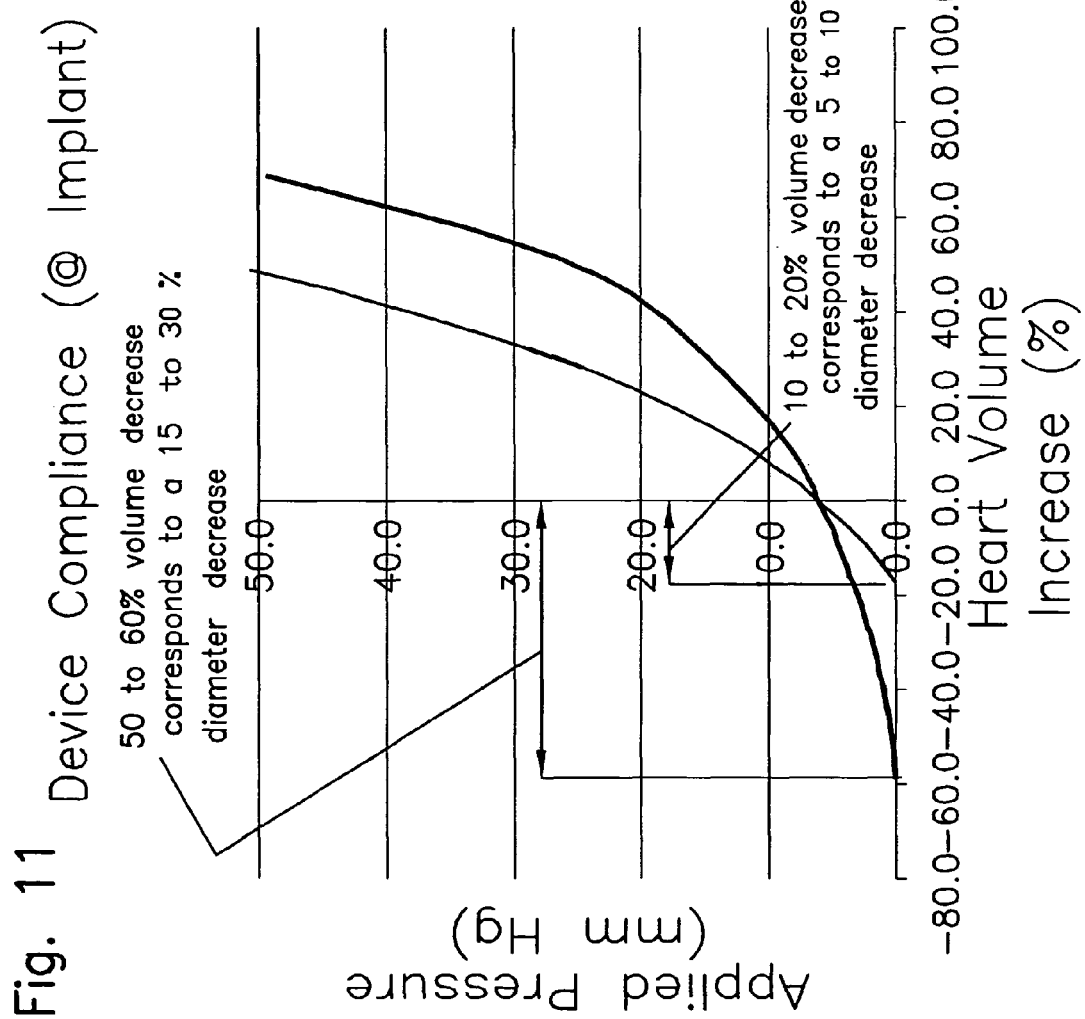
FIG. 11 shows compliance curves (pressure versus % volume change) for a lower compliance device (A) and a higher compliance device (B) at implant.

FIG. 11 shows the compliance curves of two devices as implanted over the ventricular portion of the heart. The lower compliance (A) and higher compliance (B) devices are both stretched to apply the same external pressure (approximately 6 mm Hg) to the ventricular portion of the heart at the time of implant and initial heart volume (i.e. 0% heart volume increase). The devices plotted in FIG. 11 are the same devices as shown in FIG. 10. The zero points on the horizontal axes on the two Figures are not the same. Therefore percent calculations between the Figures will differ. In FIG. 10, the zero point is an "at rest" value for the device. In FIG. 11, the zero point is after implantation. The higher compliance of the "B" device was obtained by adding more material to the device so that less yarn crimp was removed during heat setting. The lower compliance of the "A" device is indicated by a steeper line. The compliance of either device at any point of either curve can be expressed as 1/slope of the curve at that point. Thus, at implantation, the compliance of the higher compliance device (B) is 5.5%/mm Hg compared to about 2%/mm Hg for the less compliant (A) device. If the operating range of the device is assumed to be below a 20% volume increase, the compliance range is between about 3%/mm Hg and 20%/mm Hg for the highly compliant (B) device and between about 1%/mm Hg and 3.5%/mm Hg for the less compliant (A) device. In this example, the higher compliance device is approximately 3 to 6 times more compliant depending on the given condition within the operating range. As used herein, a "high compliance" device refers to a device having a compliance between about 3%/mm Hg and about 20%/mm Hg, or greater. A "low compliance" device refers to a device having a compliance between about 1%/mm Hg and about 3%/mm Hg, or lower. In FIG. 11, the devices can theoretically apply an external pressure to the heart until the heart volume decreases to the point where the compliance curve crosses 0 mm Hg. These curves are based on loading, not unloading. Therefore, as the heart volume decreases, these curves assume that both devices have 100% elastic recovery. In general, even though the two devices do not have 100% elastic recovery, for comparison purposes the higher compliance device will have better elastic recovery than the low compliance device. Whereas a "low compliance" device may have the potential to reduce the size of a heart between about 10% to about 20% in volume, a high compliance device can continue to apply an external load to the heart to achieve up to between about a 50% to about a 60% volume reduction.

Depending on the heart shape change that is assumed (i.e., cylindrical or spherical), the volume decrease for the "low compliance" device corresponds to a decrease in diameter between about 5% to about 10%. The volume decrease for the "high compliance" device similarly corresponds to a decrease in diameter between about 15% to about 30%.

Figure 13:
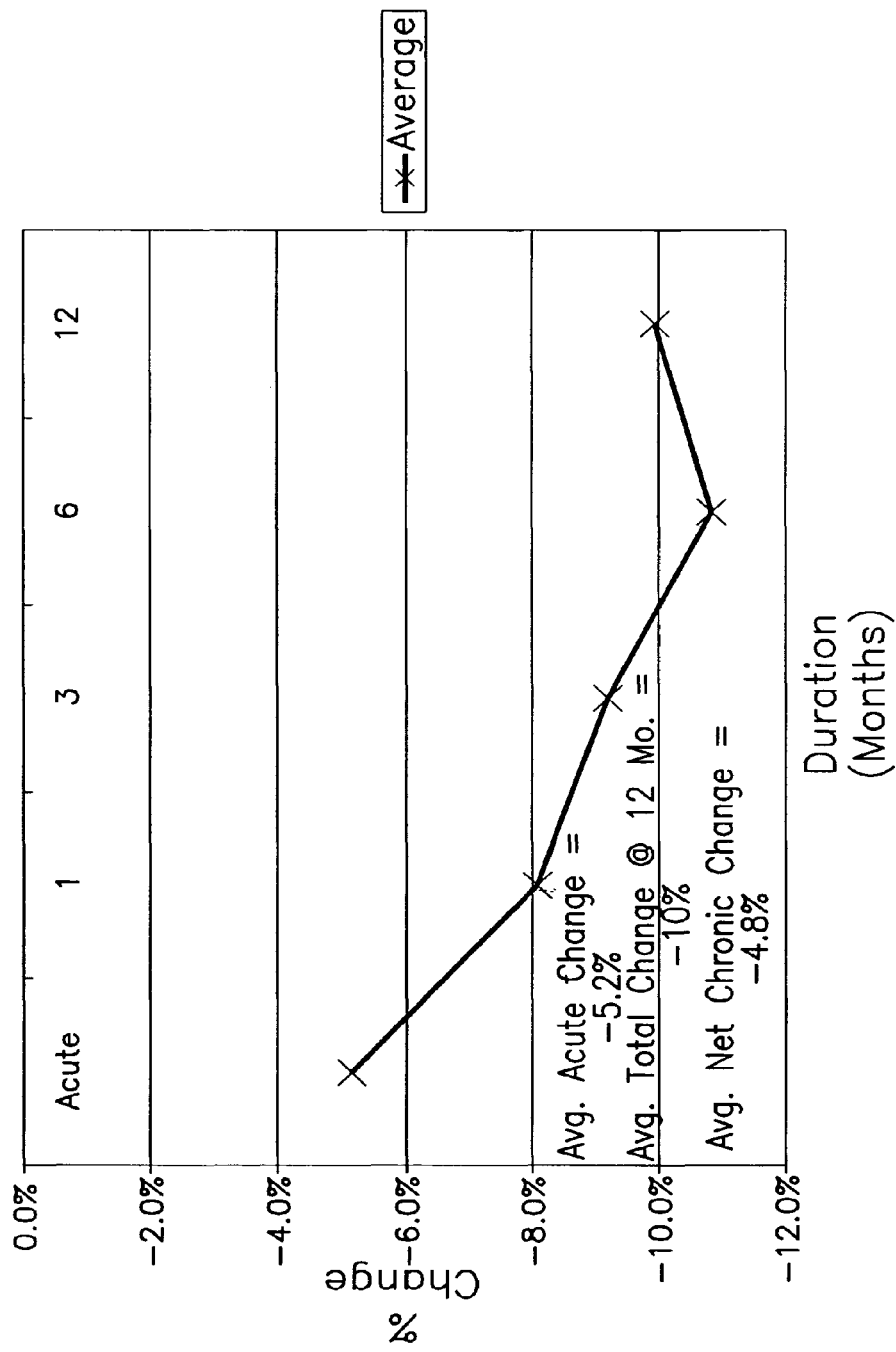
FIG. 13 is a plot of the change in left ventricle end diastolic dimension (LVEDD) over time from clinical studies.

A "low compliance device" corresponding to the lower compliance device (A) has been implanted in human clinical trails with follow-up out to 12 months post-implant (i.e., the prior knit device). FIG. 13 shows the average change in left ventricular end diastolic diameter (LVEDD) for 17 patients receiving the lower compliance device. At implant the hearts were fit to provide acute support that resulted in a 5.2% reduction in LVEDD. After 3 months post-surgery, the LVEDD decrease another 4.8% on average. This additional chronic reduction in LVEDD corresponds closely with the 5% to 10% diameter reduction of the external ventricular size predicted by the device compliance curve shown in FIG. 11 and the chronic potential energy mechanism. In fact, the amount of elastic recovery for the low compliance device has been measured in vitro to be approximately 70% to 80%, depending on the loads applied.

Figure 14:
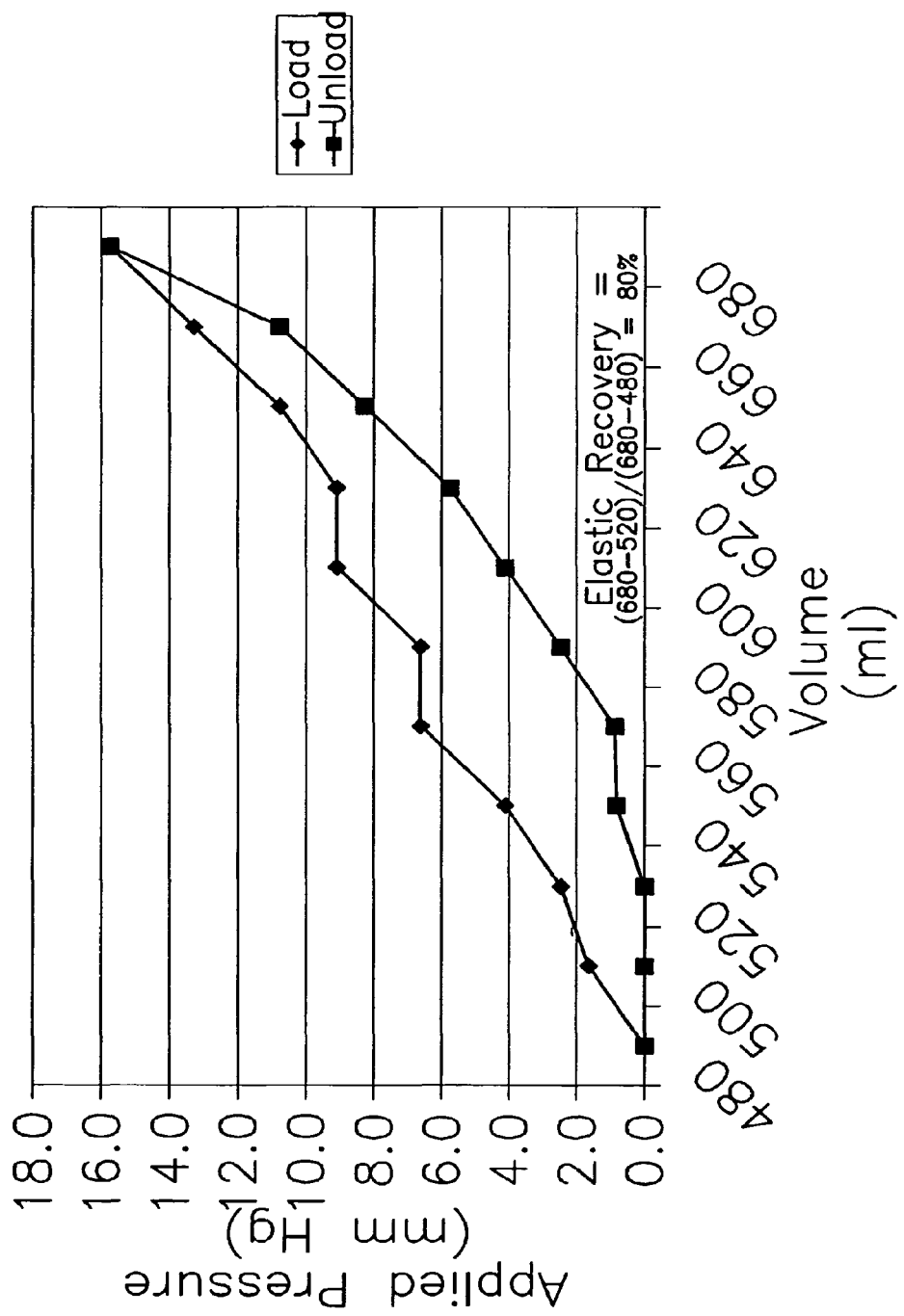
FIG. 14 is a plot of device loading (♦) and unloading (■) for determining elastic recovery.

A typical loading and unloading curve for a lower compliance device is shown in FIG. 14. The elastic recovery calculated from FIG. 14 is approximately 80%. This was calculated based on the percentage of the volume change from initial to fully deformed that was recovered (i.e. fully deformed to new unloaded resting state volume). If the predicted diameter reduction range of 5% to 8% is reduced to account for less than 100% elastic recovery, the expected decrease in diameter would be between 3.5% and 6.5%. The actual clinical result is nearly in the middle of this predicted range.

Figure 12:
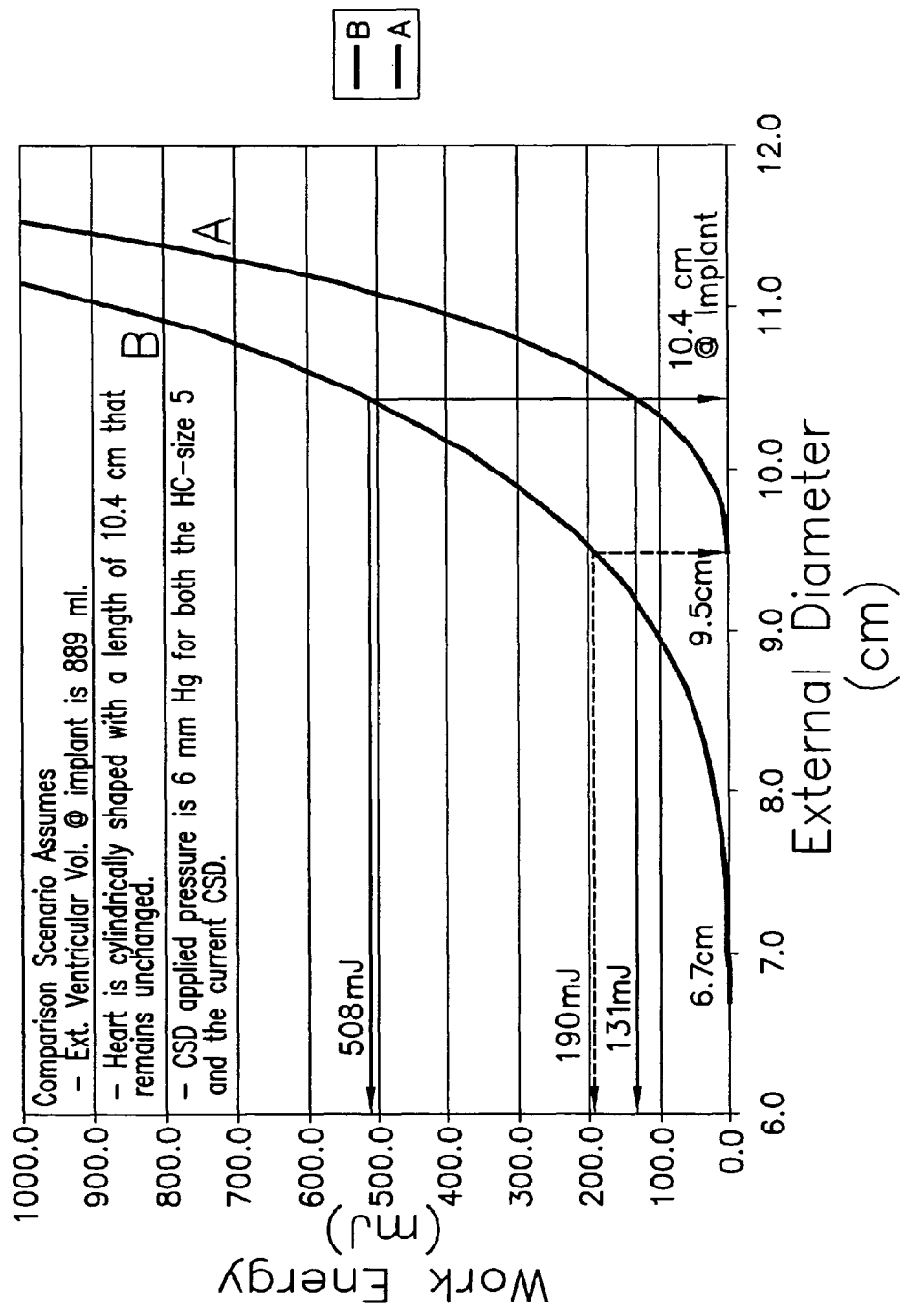
FIG. 12 is a device elastic potential energy plot comparing the work energy stored at implant for a less compliant and elastic device (A) and a highly compliant and elastic device (B)

The potential reduction in heart size attributable from the chronic potential energy release mechanism can also be examined based on the energy that is stored in the device relative to the device compliance. Elastic potential energy stored in a spring is equal to the amount of work energy (U) used to compress it if no frictional or other losses are assumed. Thus, the work energy can be determined as follows:

U=work energy=Fx/2
Where:
F=applied force=Kx
K=stiffness=1/compliance
X=displacement FIG. 12 illustrates the potential energy stored in both a low compliance (A) and high compliance (B) device at implant. Both energy curves assume that the device is implanted on the same size heart (i.e. external diameter of 8.4 cm.) with the same externally applied pressure of 6 mm Hg when implanted. The high compliant device has nearly 4 times more energy (508 mJ versus 131 mJ) at the time of implant. Although the amount of energy stored is due to the compliance, the amount available for release to reduce the heart size is based on the elastic recovery of the device. For example, if the device has 80% elastic recovery, then 80% of the energy is available to drive the heart smaller, while 20% of the energy is lost to permanent deformation of the material.

2. Eliminate Surgical Fit

As discussed previously, in one embodiment, the cardiac support device is adjusted at the time of implantation to provided the desired fit. The adjustment of the device allows it to be used on dilated hearts having a large range of shapes and sizes. To accommodate such variability in dilated hearts, the device is manufactured in many sizes. However, many dozens of sizes would be necessary to provide a sufficient selection for providing the appropriate fit across all the range of heart shapes and sizes.

One advantage of a "high compliance" jacket is that each jacket can adapt to a large shape/size range, yet still provide the appropriate fit. Since compliance is defined as the deformation for a given load, a high compliance device will result in a large change in deformation with a relatively small change in load. Thus, a target load or fit range can theoretically be accommodated by a larger displacement range with a high compliance device than for a low compliance device.

For example, two device compliance curves, low compliance (A) and high compliance (B) are shown in FIG. 10. If the chosen target fit load (i.e. pressure applied to the epicardial surface of the heart) is between about 5 mm Hg to about 7 mm Hg of pressure, the dimensional stretch range from the device resting state can be determined from the curves for each device. Device "A" can be stretched anywhere between a 17% to 23% (6% range) increase in volume from it's starting volume and will apply a 5 mm Hg to 7 mm Hg pressure. However, the higher compliance device "B" can be stretched over a larger range of 129% to 156% (27% range) from it's starting volume for the same resulting load. Now suppose it is desirable to manufacture devices that will apply a 5 mm Hg to 7 mm Hg load for heart sizes from 645 ml to 780 ml of external ventricular volume. The high compliance device (B) would require only one size to cover the range of heart sizes selected, but it would take 4 sizes of the low compliance device (A) to accommodate the heart size range. This example is illustrated in Table 2.

TABLE 2

| Device | Size (@ rest) (ml) | Min. Volume (ml) | Max. Volume (ml) | No. Device Sizes Required |
| --- | --- | --- | --- | --- |
| B | 500 | 645 | 780 | 1 |
| A | 550 | 644 | 677 | 4 |
|   | 578 | 676 | 711 |   |
|   | 607 | 710 | 746 |   |
|   | 637 | 745 | 783 |   |

Eliminating surgical fit based on a high compliance device may be beneficial for several reasons. First of all, although the surgical procedure for implanting a low compliance device is relatively simple compared to other cardiac surgeries, eliminating the fitting process would further simplify the surgery. The surgical fitting step is one of the most time-consuming steps of the surgical implant process. Eliminating this step could shorten the overall surgical time. This would result in the patient undergoing anesthesia for a shorter period of time, reducing the risks due to anesthesia dose-complications. In addition, the reduced surgical time could reduce the overall surgical costs due to a reduction in the time spent in the operating room.

Another benefit of eliminating the surgical fit is increased consistency. Surgically adjusting and fitting each device tends to introduce variability between patients by any given surgeon. In addition, there is variability between different surgeons and hospitals that can only be reduced by rigorous implant training Thus, eliminating the surgical fit procedure may reduce the variability and the training requirements.

Eliminating the surgical fit can also make implanting the device more compatible with minimally invasive surgical approaches. Typically, the surgical fit step for implant of the original device requires access to the anterior portion of the heart. This is most commonly accomplished using a full median sternotomy surgical approach. If a high compliance device can allow the appropriate fit to be obtained through device size selection rather than surgical customization of fit, the surgery: may-be possible through a smaller incision than a full median sternotomy. It may even be possible to implant the device through small portal incisions.

Minimally invasive surgical incisions can have numerous benefits, including reduced pain, less cosmetic scaring, faster hospital release and faster return to physical activities. The reduced hospital stay from minimally invasive surgery can also help to reduce overall surgical costs and make the surgery more accepted and routine in the medical community.

In one embodiment, the cardiac support device is 3-dimensional shape that is constructed from a flat fabric mesh. To form a 3-dimensional shape from a flat fabric, the device typically includes sewn seams where the device material is a little denser and thicker. Unfortunately, the seams can result in a greater tissue-response and an increased potential for adhesion between the device and adjacent tissues in the chest, other than the heart.

Thus, in another embodiment, the device is manufactured using advanced fabrication methods that eliminate the manufactured seams. However, even if the pre-fabricated seams can be eliminated, the surgical fitting may result in a seam that is even thicker and denser than those produced during device manufacture. Consequently, if the surgical seam from fitting is eliminated, for example, by using a high compliance device, and the manufactured seams are eliminated, the potential for adhesions to adjacent tissues would be reduced. This could be important, particularly when future surgeries require access to the chest cavity. Adhesions make surgical access much more difficult.

3. More Volume Overloading Tolerant

Another advantage of a high compliance device is the ability of the device to expand and not over restrain the heart in the case of volume overloading. For example, excessive fluid intake can impact the volume of the heart. A high compliance device may benefit the patient by helping to support the increased volume loading, without overly restricting the heart as might occur with the cardiac condition known as constriction. Although dilatation constraint is a potentially important mechanism of the cardiac support device, higher compliance may provide adequate support and resistance to dilatation without overly restricting the patient's normal variations in fluid intake.

Having disclosed the invention in a preferred embodiment modifications and equivalents will become apparent to those skilled in the art. It is intended such modifications and equivalents shall be included within the scope of the appended claims. For example, while the invention is described covering the ventricles, the invention can cover one or both of the atria only or in combination with ventricle coverage. Also, the device can be provided with circumferential fibers which have a maximum stretch (or no stretch) at a volume representing a maximum volume for end diastole at time of placement. Such a modification provides acute prevention of diastolic expansion beyond a maximum. Use of multiple sets of fibers are described in Haindl international patent application PCT WO 98/58598 published Dec. 30, 1998.

The invention claimed is:

1. A device for treating diseases of a heart, the device comprising: a biocompatible material configured to cover an external surface of the heart; the material having a compliance reflecting an ability to deform under strain to a stretched state, and an elasticity reflecting a tendency to return to a rest state from the stretched state; the material having a rest size at the rest state and a stretched size at the stretched state, the stretched size being at least 20% greater than the rest size; the elasticity and compliance being selected to store energy in the material to assist chronic remodeling of the heart and avoid significant acute resistance to diastolic filling of the heart, and wherein the compliance is greater than a compliance of a normal myocardium, the compliance being the inverse of stiffness, and wherein the biocompatible material conforms to the external surface of the heart and is sized to provide resistance to circumferential expansion of the heart without impeding systolic contraction; and wherein the material has a stiffness of less than about 3.8 lbs/in (0.68 kg/cm) when subjected to a uniaxial load at a strain of less than 30%.

2. The device according to claim 1, wherein the rest size defines a rest volume and the stretched size defines a stretched volume.

3. The device according to claim 2, wherein the material is configured as a jacket having an upper and a lower end, the upper end defining an opening for receiving the heart.

4. The device according to claim 3, wherein the material is closed at the lower end.

5. The device according to claim 3, wherein the material is open at the lower end.

6. The device according to claim 2, wherein the compliance allows at least a 3% increase in volume for every 1 mm Hg change in applied pressure.

7. The device according to claim 1, wherein the rest size defines a rest surface area and the stretched size defines a stretched surface area.

8. The device according to claim 7, wherein the material is configured as a patch.

9. The device according to claim 1, wherein the compliance is greater than a compliance of a normal latissimus dorsi, the compliance being the inverse of stiffness, and wherein the biocompatible material conforms to an external surface of the heart and is sized to provide resistance to circumferential expansion of the heart without impeding systolic contraction.

10. The device according to claim 1, wherein the material is sized to be larger than the external surface of the heart to which it is applied, and is adapted to be sized by adjustment during implantation.

11. The device according to claim 1, wherein the material is capable of an elastic recovery of at least about 50%.

12. A device for treating diseases of a heart, the device comprising: a biocompatible material configured to cover an external surface of the heart; the material having a compliance reflecting an ability to deform under strain to a stretched state, and an elasticity reflecting a tendency to return to a rest state from the stretched state; the material having a rest size at the rest state and a stretched size at the stretched state, the stretched size being at least 20% greater than the rest size; the elasticity and compliance being selected to store energy in the material to assist chronic remodeling of the heart and avoid significant acute resistance to diastolic filling of the heart; and wherein the biocompatible material has a stiffness of less than 0.5 lbs/in (0.09 kg/cm) when subjected to a uniaxial load at a strain of less than 30%.

13. A device for treating diseases of a heart, the device comprising: a biocompatible material configured to cover an external surface of the heart; the material having a compliance reflecting an ability to deform under strain to a stretched state, and an elasticity reflecting a tendency to return to a rest state from the stretched state; the material having a rest size at the rest state and a stretched size at the stretched state, the stretched size being at least 20% greater than the rest size; the elasticity and compliance being selected to store energy in the material to assist chronic remodeling of the heart and avoid significant acute resistance to diastolic filling of the heart; and wherein the material is sized to be smaller than the external surface of the heart to which it is applied, wherein the material is configured to exert a pressure on the external surface of the heart that is no greater than an end diastolic pressure of a right ventricle of the heart.

14. A device for treating diseases of a heart, the device comprising: a biocompatible material configured to cover an external surface of the heart; the material having a compliance reflecting an ability to deform under strain to a stretched state, and an elasticity reflecting a tendency to return to a rest state from the stretched state; the material having a rest size at the rest state and a stretched size at the stretched state, the stretched size being at least 20% greater than the rest size; the elasticity and compliance being selected to store energy in the material to assist chronic remodeling of the heart and avoid significant acute resistance to diastolic filling of the heart; and wherein the material is configured to apply a pressure to the external surface of the heart at end diastole of less than 10 mm Hg.

* * * * *